United States Patent [19]

Oberhardt

[11] Patent Number: 4,849,340
[45] Date of Patent: Jul. 18, 1989

[54] REACTION SYSTEM ELEMENT AND METHOD FOR PERFORMING PROTHROMBIN TIME ASSAY

[75] Inventor: Bruce Oberhardt, Raleigh, N.C.

[73] Assignee: Cardiovascular Diagnostics, Inc., Durham, N.C.

[21] Appl. No.: 33,817

[22] Filed: Apr. 3, 1987

[51] Int. Cl.[4] ................... G01N 1/12; G01N 33/553; B01L 3/00; C12M 1/14
[52] U.S. Cl. .......................................... 435/13; 435/7; 436/69; 436/517; 436/525; 436/526; 422/57; 422/58; 422/73; 422/110; 73/863.71; 73/864.72
[58] Field of Search ............................ 435/7, 13, 310; 436/517, 525, 526, 809, 46, 69; 422/57, 58, 73, 102, 110, 292; 73/863.71–863.73, 864.72

[56] References Cited

U.S. PATENT DOCUMENTS

| | | | |
|---|---|---|---|
| Re. 27,866 | 1/1974 | Adler | 422/73 |
| 2,616,796 | 11/1952 | Schilling et al. | 435/296 |
| 3,233,975 | 3/1962 | McCormick | 422/73 |
| 3,395,210 | 7/1968 | Lenahan et al. | 424/2 |
| 3,434,859 | 3/1969 | Benjamin | 117/17 |
| 3,450,501 | 6/1969 | Oberhardt | 422/73 |
| 3,520,659 | 7/1970 | Steinberg et al. | 422/73 |
| 3,635,678 | 1/1972 | Seitz et al. | 422/73 |
| 3,650,698 | 3/1972 | Adler | 422/73 X |
| 3,690,836 | 9/1972 | Buissiere et al. | 23/253 |
| 3,691,017 | 9/1972 | Brown et al. | 195/103.5 R |
| 3,695,842 | 10/1972 | Mintz | 23/230 R |
| 3,836,333 | 9/1974 | Mintz | 23/259 |
| 3,861,197 | 1/1975 | Adler | 436/69 |
| 3,880,714 | 4/1975 | Babson | 195/99 |
| 3,918,908 | 11/1975 | Moyer et al. | 436/69 |
| 4,062,652 | 12/1977 | Rolfo-Fontana | 422/61 |
| 4,088,448 | 5/1978 | Liija et al. | 422/102 |
| 4,233,029 | 11/1980 | Columbus | 23/230 R |
| 4,252,536 | 2/1981 | Kishimoto et al. | 356/36 |
| 4,302,313 | 11/1981 | Columbus | 204/195 R |
| 4,310,399 | 1/1982 | Columbus | 204/195 R |
| 4,321,057 | 3/1982 | Buckles | 435/4 |
| 4,323,536 | 4/1982 | Columbus | 422/58 X |
| 4,340,669 | 7/1982 | Bauer | 435/14 |
| 4,344,438 | 8/1982 | Schultz | 128/634 |
| 4,391,905 | 7/1983 | Bauer | 435/14 |
| 4,391,906 | 7/1983 | Bauer | 435/14 |
| 4,413,407 | 11/1983 | Columbus | 29/825 |
| 4,426,451 | 1/1984 | Columbus | 436/518 |
| 4,473,457 | 9/1984 | Columbus | 204/416 |
| 4,477,575 | 10/1984 | Vogel et al. | 422/57 X |
| 4,558,014 | 12/1985 | Hirschfeld et al. | 436/527 |
| 4,582,684 | 4/1986 | Vogel et al. | 422/57 |
| 4,596,695 | 6/1986 | Cottingham | 422/58 |
| 4,654,127 | 3/1987 | Baker et al. | 204/1 T |
| 4,678,757 | 7/1987 | Rapkin et al. | 422/56 X |
| 4,682,895 | 7/1987 | Costello | 422/58 X |
| 4,712,460 | 12/1987 | Allen et al. | 83/208 |
| 4,731,330 | 3/1988 | Hill et al. | 436/16 |
| 4,753,776 | 6/1988 | Hillman et al. | 422/101 |
| 4,756,884 | 7/1988 | Hillman et al. | 422/73 |

FOREIGN PATENT DOCUMENTS

| 3523439 | 1/1987 | Fed. Rep. of Germany | 422/56 |
|---|---|---|---|
| WO86/00141 | 1/1986 | PCT Int'l Appl. | 435/7 |
| 2168808 | 6/1986 | United Kingdom | 422/73 |

OTHER PUBLICATIONS

"Coumadin Control at Your Fingertips".
Anal. Chem., (1980), vol. 52, pp. 864–869, "Fiber Optic pH Probe for Physiological Use", John I. Peterson et al.
Columbus et al., *Clin. Chem.* 33/9, 1531–1537 (1987) "Architextured" Fluid Management of Biological Liquids.

Primary Examiner—Robert J. Warden
Assistant Examiner—Carol A. Spiegel
Attorney, Agent, or Firm—Oblon, Spivak, McClelland, Maier & Neustadt

[57] ABSTRACT

An element and method for easily performing liquid assays are disclosed. The element uses capillary action to draw a predetermined volume of a liquid sample into a reaction chamber charged with reagent, where reaction between the liquid sample and the reagent is monitored.

16 Claims, 19 Drawing Sheets

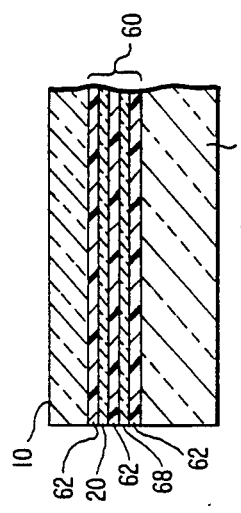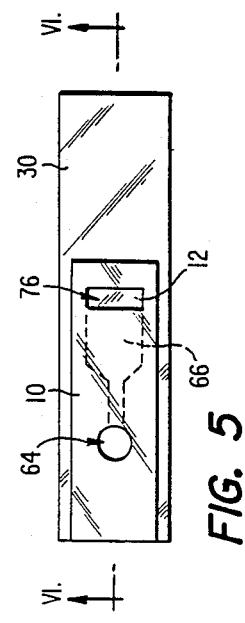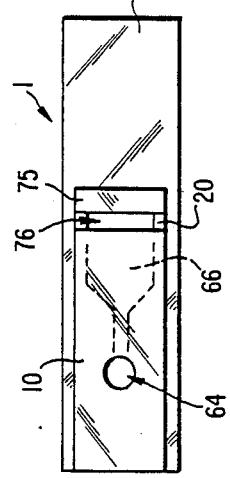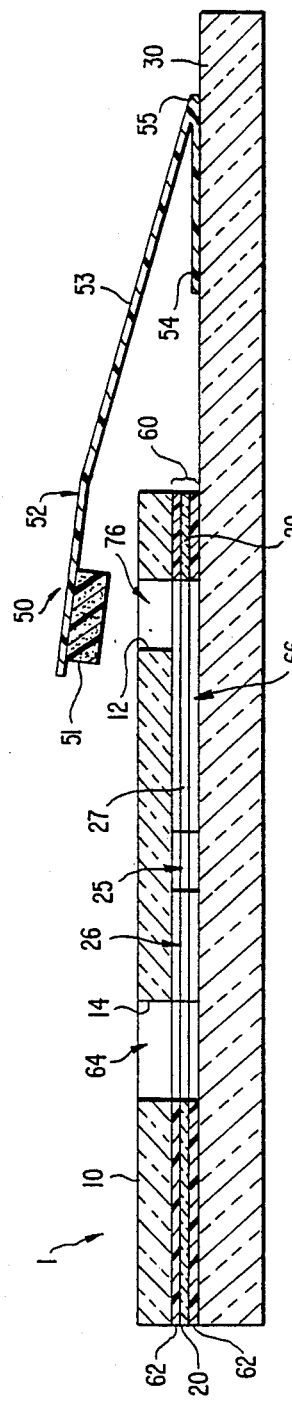

LEVEL I     LEVEL II     LEVEL III     LEVEL IV

REACTION SYSTEM ELEMENT AND METHOD FOR PERFORMING PROTHROMBIN TIME ASSAY

BACKGROUND OF THE INVENTION

1. Field of the Invention

The present invention relates to disposable reagent-containing elements which can be used in conjunction with an electronic instrument for performing diagnostic assays (medical diagnostics). It also relates to a method for performing diagnostic biological assays employing the use of a disposable reagent-containing element.

2. Discussion of the Background

Many analytical techniques have been developed for chemical, biochemical and biological assays. Procedures that use a discrete fluid sample for the analysis of a single analyte are traditionally characterized as wet chemical techniques or dry chemical techniques. In recent years both types of techniques have been automated to reduce costs and simplify procedures. Wet chemical methods, typified by the TECHNICON® autoanalyzers, utilize batches of reagent solutions, pumps and fluid controls, coupled with conventional sensors such as radiometric (e.g.: fluorescent, colorimetric, or nephelometric) electrochemical (e.g.: conductometric, polarographic, or potentiometric) and others, such as ultrasonic, etc. sensors. These techniques are characterized by large equipment, and are generally expensive. They are complicated, and require a skilled operator.

Decentralized testing, particularly in medical applications, has been achieved with a variety of simpler systems often based on cuvettes for optical determination but sometimes based on dry chemistry-based "reagent strip" technology. Generally, a reagent strip is an absorbent structure containing a reagent which self-meters an applied sample and develops or changes color to indicate the extent of reaction. Although self metering, some reagent strips, however, require pipetting of sample to achieve maximum accuracy and precision. A reagent strip is employed either by itself or in conjunction with a simple instrument to read the color intensity or hue and translate the results into a numerical value which is displayed. Unlike a cuvette or test tube, mixing or convection cannot be sustained in a reagent strip after the sample has entered, and once having entered, the sample cannot be removed from within without destroying the integrity of the strip. In one application, reagent strip technology is used extensively in the home by diabetic patients who test themselves daily to determine blood sugar levels.

In a more general example of "reagent strip" technology, Eastman Kodak has introduced a system of dry chemistry, claiming to overcome many of the traditional weaknesses of dry chemical methods. The Kodak technique utilizes flat, multi-layered sheets arranged in sequence. The top layer receives a liquid sample which passes downward undergoing separation and reactions in a pre-arranged sequence. The sheet is designed to accept a small volume of liquid and distribute it uniformly over a reproducible area. The area is less than the total area of the multi-laminar sheet. Each layer of the sheet is essentially homogenous in a direction parallel to the surface. Once the sample has spread radially (a rapid process), the components of the liquid can move downward at rates that are essentially the same in any plane that is parallel to the surface. In this way uniform reactions, filtrations, etc. can occur.

The analyte is detected in the multi-layered sheets by radiometric or electrochemical methods which are carried out in a thermostated environment. This permits the use of kinetic and static measurements to detect analyte concentrations in a liquid sample.

Radiation is caused to enter this assembly in a path which is traverse to the several layers. The radiation is modified by the analyte or by a component or product of the analyte. For example, the exciting radiation may be partially absorbed by the analyte or by a component or product of the analyte. The modified radiation may be reflected back transversely through the laminar assembly, typically from a reflective layer, adjacent or nearly adjacent to a thin layer where color is formed. Thus, reflectance can be monitored (as opposed to transmission only through the color producing layer). Reflectance, as expressed by Kubelka-Monk theory, consists of optical density absorbance and scattering components and is more sensitive than transverse colorimetry through a thin, turbid layer. Reflectance, however, may be a more difficult technique to standardize and to interpret data from than colorimetry.

Conventional colorimetry has not been practiced with reagent strips because the color producing layers are generally thin and not transparent. The path of the exciting radiation is thus very short (with large light losses due to opacity) and is determined by the thickness of the layer in which the exciting radiation encounters the substance which is excited. Since this dimension must be very small to permit rapid measurement, e.g., 10 $\mu$m to 100 $\mu$m, the degree of modification of the exciting radiation is quite small. This limits the applicability of this technique to analyses in which the analyte (or the product of the analyte) interacts very strongly with the exciting radiation, otherwise a very sensitive detecting apparatus has to be used. This method has been shown to be useful for measuring analytes in blood that exist at relatively high concentrations, e.g., glucose, BUN, cholesterol and albumin.

Other analytical methods have been developed that utilize rapidly reversable chemical reactions to continuously monitor analyte concentrations in biological fluids, or industrial effluent streams, or ponds, lakes and streams. For example, several methods have been proposed to measure the oxygen level in blood of critically ill patients.

Reagent strip technology, however, possesses salient drawbacks and limitations. For example, once a sample is added to a reagent strip and permeates the porous structure of the strip, the sample cannot be removed or washed out without destroying the integrity of the strip. For example, immunoassays are extremely difficult to perform with reagent strips, in part because separation of free and bound antigen (or antibody) molecules from a mixture of both cannot be readily achieved in a conventional porous or layered structure. This limits possible immunoassay applications to certain special cases of reactions, for example certain homogenous reaction sequences. Incubation with mixing, a step common to a variety of assays, cannot be performed easily in conventional reagent strip formats since they rely on diffusion and initial capillary action only for mixing.

Technologies have not yet been developed to cause or to control forced convection for a specified period of time within the porous structure of a reagent strip after the sample has entered and permeated the porous strip structure. In conventional reagent strips, the strip is an absorbant matrix in which mixing is extremely difficult and limited. In addition, reagent strips almost exclusively use reflectance as a photometric method to quantitatively determine the extent of a color reaction. There are no reagent strips known to the inventor which can be read via light transmission/absorbance colorimetry, nephelometry, fluorescence, chemiluminescence, or evanescent wave technology. Fluorescence measurement is possible in reagent strips, but difficult to achieve. Electrochemistry has been used successfully.

As discussed above, a large number of types of medical tests are carried out by trained medical laboratory personnel. These tests must be performed accurately and reproducibly with a minimum amount of error since they are used as aids in diagnosing and treating medical ailments. To aid laboratory personnel in performing these tests accurately on a large number of samples in a relatively short period of time, auxiliary equipment, which is often expensive, is frequently used. Most of these tests are performed on a macro scale and thus require considerable quantities of both sample and reactants. They also require varying degrees of sample preparation. These and other reasons are major contributors to the generally relatively expensive nature and sources of error in medical diagnostic tests performed on body fluids.

Improvements have been made in some medical tests. For example, the reagent strip technology discussed previously simplifies medical tests, minimizes the required quantities of sample and/or reactants, can minimize possible sources of error, and lower costs. Various types of medical tests, however, have been difficult to perform accurately and economically on either a macro or a micro scale. In this respect, medical tests which require rapid and thorough mixing of reagents with a sample to provide a clearly defined starting point, an accurate measurement of reaction time, and a clear determination of the reaction endpoint, have been particularly difficult to perform with simple and inexpensive devices and have been plagued with inaccuracies resulting from errors in measurement and manipulation.

Once such type of test is the blood prothrombin time test ("PT" hereinafter). This test measures the time required to form a blood clot (via extrinsic and intrinsic blood coagulation physiologic pathways).

Coagulation assays, in general, are used for a variety of reasons. They are principally used for monitoring patients receiving anticoagulant therapy. The most frequently performed coagulation assay is PT. Prothrombin time determinations are used to monitor patients receiving oral anticoagulants such as warfarin. An accurate monitoring of coagulation in these patients is important to prevent recurrent clotting (thrombosis) and to keep the coagulation mechanism sufficiently active to prevent internal bleeding. Prothrombin time testing provides information to permit better drug control to be achieved through the regulation of drug dosage.

In conventional practice, PT assays are performed by the addition of a liquid reagent to a plasma sample. The reagents are typically supplied in dried form and consist primarily of thromboplastin and calcium chloride. The dried reagent is reconstituted before use by addition of a measured amount of distilled water. The reagent is thermally sensitive, and refrigeration prior to use is required. The shelf life of the reagent in dried form is from one to two years. However, when it is reconstituted the reagent is considerably more labile and must be used within a few hours or discarded. In some cases reconstituted reagents can be kept for a few days under refrigeration.

Prothrombin time assays are performed by mixing sample and reagent at 37° C., and monitoring the progress of the reaction until a perceptible clot (or "gel clot") is detected. The development of a gel clot is the end point of the reaction. This end point may be detected in various ways; by viscosity change, by electrode reaction; and, most commonly, by photometric means. The test result is generally compared to a result using a normal (control) plasma.

Before performing the test, the blood sample is collected in the tube or syringe containing anti-coagulant (citrate). The blood sample is centrifuged, and the plasma separated (e.g., by decantation) from the red blood cells. A measured quantity (usually 0.1 ml) of plasma is pipetted into the reaction vessel or cuvet. A measured amount of reagent is then added manually via pipette or automatically by means of other volumetric delivery systems capable of metering a known, preset quantity of reagent. Alternatively, the sample can be added to the reagent directly. Typically, 0.2 ml of reagent is employed. The addition of the reagent initiates the reaction.

Some PT kits for use in the home are known. For example, McCormick (U.S. Pat. No. 3,233,975) discloses a prothrombin reaction chamber. The chamber is constructed of a transparent material so that the progress of the reaction can be visually monitored. To perform a blood prothrombin time test with this chamber, one adds sequentially a measured volume of a prepared blood sample and a measured volume of an aqueous solution of reagent to the chamber. The chamber is then manually agitated, and the progress of the reaction visually monitored and timed with a stop watch.

This prothrombin reaction chamber, however, suffers from numerous disadvantages. For the prothrombin test to be performed with this reaction chamber, a prepared blood sample is used. Thus sample manipulation is required. A specific volume of the prepared blood sample must be added to the chamber. The measurements involved in obtaining this specific volume of prepared blood sample contribute inaccurate results and considerable labor.

This reaction chamber also requires the preparation of a solution containing the reagent(s). The precise measurement of the amounts of materials and water to be combined in preparing the reagent solution introduces another additional source of error. The measurement of the quantity of reagent solution to be added to the chamber provides a further source of error. Moreover, as discussed above, having to use a reagent solution is undesirable because of potential stability problems. If the reagent solution is not used within a few hours, the solution must be discarded.

McCormick's prothrombin reaction chamber is based on the visual observation of the reaction to measure clotting time. It does not permit accurate monitoring of sample mixing with the reagent(s), accurate determination of reaction starting point (which is as important as the end point when reaction time is being measured), or accurate determination of reaction end point.

Accordingly there is a strongly felt need for a facile and accurate method for the performance of biological assays, e.g., in medical application. Such method should be based on a minimum number of manipulations of either a sample or reagent.

Ideally it should require no sample or reagent-containing solution preparation. It should minimize problems associated with reagent instability and optimize accuracy. It should permit effective mixing of sample and reagent. It should permit sample manipulation. It should require only a very small amount of sample. And it should be able to perform automatic treatments of the sample, e.g., separate red blood cells from plasma in blood. This method should be based on a simple and inexpensive reagent-containing element.

SUMMARY OF THE INVENTION

Accordingly, it is an object of this invention to provide a facile method for the performance of assays, e.g., biological assays.

It is another object of this invention to provide a facile and accurate method for the performance of assays, e.g., biological assays.

It is another object of this invention to provide a method for the performance of assay where the method is based on a minimum number of manipulations of either sample or reagent.

It is another object of this invention to provide a method for the performance of assays requiring no preparation of sample or reagent-containing solution.

It is another object of this invention to provide a method for the performance of assays which minimizes problems associated with reagent instability.

It is another object of this invention to provide a method for the performance of assays in which accuracy is optimized.

It is another object of this invention to provide a method for the performance of assays permitting an effective mixing of sample and reagent(s).

It is another object of this invention to provide a method for the performance of assays permitting sample manipulation.

It is another object of this invention to provide a method for the performance of assays requiring only a very small amount of sample.

It is another object of this invention to provide a method for the performance of assays permitting the automatic treatment of the sample, e.g., separation of the red blood cells from plasma and blood.

It is an object of this invention to provide a novel element which permits the facile and accurate performance of diagnostic assays.

It is another object of this invention to provide such an element which can be used in diagnostic assays without requiring the preparation of a reagent solution from dry reagent.

It is another object of this invention to provide such an element permitting the accurate testing of samples with minimum sample manipulation.

It is another object of this invention to provide a novel element for performing a diagnostic assay in which no measurement of sample or reagent is required for performance of the assay.

It is another object of this invention to provide a novel element for performing a diagnostic assay permitting an optimization of accuracy.

It is another object of this invention to provide a novel element for performing a diagnostic assay permitting the effective mixing of sample and reagent(s).

It is another object of this invention to provide a novel element for performing a diagnostic assay permitting sample manipulation.

It is another object of this invention to provide a novel element for performing a diagnostic assay requiring only a very small amount of sample.

It is another object of this invention to provide a novel element for performing a diagnostic assay capable of automatically treating the sample, e.g., separating red blood cells from plasma and blood.

Surprisingly, all of these objects, and other objects which will become obvious from a description of the invention provided hereinafter, have all been satisfied with the discovery of the present reagent-containing element for performing diagnostic biological assays. This element comprises a channel structure defining a sample well and a reaction volume in communication with each other. The channel structure possesses a geometry which causes a liquid sample placed into the sample well to be drawn into and fill the reaction volume via capillary action, wherein after the reaction volume is filled, the liquid sample remains stationary.

In the assembly of this element, the element can comprise a base, an overlay, and a cover. The base comprises a major surface. The overlay is situated on the base. The cover is situated on the overlay, opposite the base. The overlay comprises a channel structure defining a sample well and a reaction space in communication with each other. The cover comprises a means for adding a sample to be analyzed to the sample well.

The assay is performed by monitoring a reaction of the sample in the reaction space with the sample as a whole being stationary during essentially all of the assay. After the assay, or to permit manipulation of the sample, the sample can be removed from the reaction volume, but the geometry of the present element provides for the immobility of the sample once the reaction volume has been filled.

Although the element can comprise the base, overlay and cover assembly described above, it can be produced by using any material forming technique which will produce the desired geometry. Thus, instead of assembling the base, overlay and cover as separate components, the element can be produced by assembling either fewer or a greater number of components. For example, the element can be produced by injection molding whereby one obtains two pieces which when assembled produce the element of this invention.

In certain embodiments, the element also comprises a means for channelling light from an outside source to the reaction chamber. This means is referred to as a waveguide in this text. Such an element is used with a means for detecting light emitted from the reaction chamber. Other embodiments measure non-optical properties of the sample. Such measurements may, for example, be conductometric, polarographic or potentiometric in nature, or may involve a combination of the above.

Of course, the present invention also provides a novel method for performing a diagnostic assay. This method is based on using the reagent-containing element of this invention. The assays which can be performed are all liquid system assays, i.e., assays using liquid media. A specific example of such assays is biological assays.

An element containing a measured amount of at least one reagent situated in the reaction space of the element, is used. A biological sample is added to the sample well of the reagent-containing element. The geometry of the reagent-containing element forces a specific volume of the biological sample to be drawn from the sample well by capillary action to the reaction space. In the simplest case of reagent containment, once the sample enters the reaction space it contacts the reagent, dissolving the reagent. Using the means for channelling light from an outside source to the reaction chamber, light is impinged upon the reaction space during the whole process. Light emitted from the reaction space is monitored, permitting monitoring of the dissolution process, the progress of the reaction, the end of the reaction, and a determination of reaction time.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein like reference numerals designate identical or corresponding parts throughout the several views.

FIG. 5 is a top view of the elements of FIGS. 1-3, when assembled.

FIG. 6 is an elevational longitudinal cross-section of a first embodiment of a reaction slide according to the current invention, the cover, overlay and base being sectioned along line VI—VI of FIG. 5.

FIG. 7 is an elevational cross-section of a fragment of a reaction slide according to the current invention, illustrating a modification in which the reaction slide comprises a spacer that includes two overlays.

FIG. 8 is a top view of a second embodiment of a reaction slide according to the current invention.

FIGS. 65 and 66 illustrate apparatus that may be used in conducting a Plasminogen Activator assay.

DETAILED DESCRIPTION OF THE PREFERRED EMBODIMENTS

Figure 1:
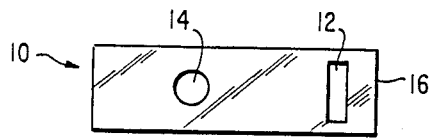
FIG. 1 is a top view of a cover of a first embodiment of a reaction slide according to the current invention.
Figure 2:
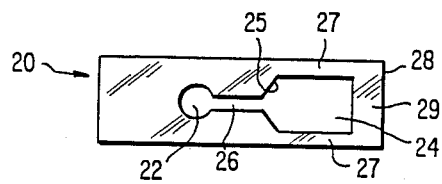
FIG. 2 is a top view of an overlay of a reaction slide according to the first embodiment.
Figure 3:
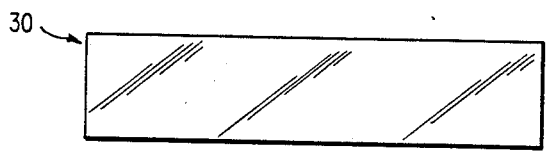
FIG. 3 is a top view of a base of a reaction slide according to the first embodiment.

Shown in FIG. 1 is a top view of a cover 10 of a first embodiment of a reaction slide according to the current invention. Shown in FIG. 2 is a top view of an overlay 20 of the first embodiment. Shown in FIG. 3 is a top view of a base 30 of the first embodiment.

Figure 4:
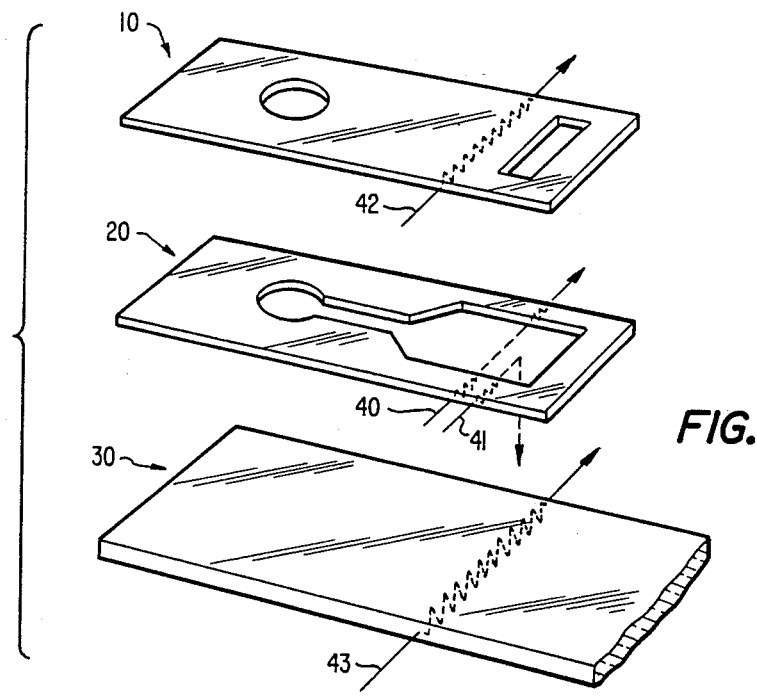
FIG. 4 is an exploded perspective of the items shown in FIGS. 1-3, the elements being oriented as in the assembled reaction slide.

FIG. 4 is an exploded view showing the relative positions of the cover 10, overlay 20 and base 30.

FIG. 5 is a top view of the cover 10, overlay 20 and base 30, when assembled.

FIG. 6 is a longitudinal vertical cross-section of a first embodiment of a reaction slide 1 according to the current invention. The cover 10, overlay 20 and base 30 are sectioned along line VI—VI of FIG. 5. As will be described more fully below, the reaction slide 1 contains certain elements in addition to those shown in FIGS. 1–5.

Now referring generally to FIGS. 1–6, the cover 10 comprises a thin glass or polymeric sheet, typically transparent, having formed therein a sample receiving opening 14 and an elongate opening 12 proximate a distal end 16 of the cover.

The overlay 20 comprises a thin glass or polymeric sheet, typically transparent, having formed therein a cut-out, the cut-out having a geometry as shown to form a sample receiving opening 22, a reaction space 24 and a conduit 26 communicating the reaction space and the sample receiving opening. (The reaction space 24 becomes a reaction volume upon assembly of the cover, overlay and base.) Advantageouly, tapering walls 25 form a transition between the conduit 26 and reaction space 24. The distal end 28 of the overlay is closed as shown at 29.

The base 30 comprises a sheet of glass or polymeric material, typically transparent and typically somewhat thicker than either the cover 10 or overlay 20.

The cover 10 and base 30 are separated by a spacer 60 (FIG. 6), the spacer 60 being made up of the overlay 20 sandwiched between two adhesive layers 62 which respectively join the overlay 20 to the cover 10 and the overlay 20 to the base 30. Each of the adhesive layers 62 has the same shape as the overlay 20. That is, each of the adhesive layers is formed with an opening having a shape corresponding to the sample receiving opening 22, the reaction space 24 and the conduit 26 of the overlay 20. Accordingly, there are formed in the reaction slide a sample well 64, a reaction volume 66, a conduit communicating the reaction volume 66 and the sample well 64, and a vent 76 formed by the opening 12 in the cover 10 communicating the reaction volume 66 with the environment of the slide.

The bottom surface of the cover 10, facing the base 30, is spaced from the top surface of the base 30 by a distance that is sufficiently small to cause a sample placed in sample well 64 to be drawn into the reaction volume 66 by capillary action. Such action is made possible by the presence of the vent 76.

As shown in FIG. 5, the length (left to right in the drawing) of the cover 10 is the same as that of the overlay 20, and the width (top to bottom in the drawing) of the cover 10 nd overlay 20 are the same and are less than that of the base 30.

Preferably there is provided a liquid absorbing matrix (LAM) for withdrawing fluid from the reaction space when desired. To this end, there may be provided as shown in FIG. 6 a LAM assembly 50 including a LAM pad 51, illustrated as a sponge, fixed on a LAM support 52, the LAM support 52 comprising an arm 53, a tab 54 fixed on the base 30, and a living hinge 55 joining the arm 53 and tab 54. When the arm 53 is pressed downwardly, manually or by an automated presser (not shown), the LAM 51 will enter the vent 76 and make contact with fluid in the reaction volume 66, thereby drawing out the fluid. It has been found that, when the cover 10 is made of a polymeric material, this withdrawing action may be enhanced by downward deflection of a portion of the cover 10 adjacent the vent 12. It would appear that this enhanced withdrawal is caused by a localized narrowing of the distance between the cover 10 and base 30, thereby creating a narrowed passage to enhance capillary action. Thus although the cover 10 can be made of either rigid of flexible material, in this embodiment of the invention, the cover 10 is preferably made of a flexible material.

Observations and measurements of chemical reaction occurring within the reaction volume 66 may be made by a number of methods, as described more fully below. At present, optical methods are preferred, but the choice of method will depend upon the assay being performed. Shown in FIG. 4 are a number of paths that light may typically follow for making such measurements and observations. These paths may be used alone or in combination.

In light path 40, light is introduced through a side of the overlay 20 and passes initially through a portion of the overlay disposed between the closed end 29 and tapering wall 25. This portion of the overlay and its opposite corresponding portion will be referred to as internal waveguides 27. Thereafter, the light passes through the reaction volume 66 and out through the opposite waveguide 27. As illustrated schematically, light passing in this direction through the waveguides is internally reflected off the top and bottom surfaces of the overlay 20. Light path 40 is useful in making measurements based on the transmission or absorbance of light by the fluid within the reaction volume 66, in which case there is measured the ratio of light intensity before and after passing through the sample in the absence of scattering or excluding scattering. The Beer-Lambert Law describes the phenomenon. Standard detectors are employed in a line of sight configuration with the light source.

Light path 41 illustrates a measurement that may be made based upon light scattering in which light is first introduced transversely through an internal waveguide 27, enters the reaction volume 66, is then scattered by the sample, a portion of the scattered light proceeding downwardly through the base 30 and then leaving the reaction slide. Light scattering measurements or nephelometry measures light which is not irreversibly absorbed by the sample and emerges at various angles, the spatial/intensity distribution being dependent upon particle size, shape and wavelength of the excitation energy. Rayleigh and Mie theories are useful models. Standard detectors are employed. Examples are photocells or photomultipliers, the latter being employed at very low light levels. Excitation source wavelength may be fixed at a particular value. The detector is typically set at a predetermined angle from the direction of excitation.

Light paths 42 and 43 respectively show light entering laterally through the sides of the cover 10 and base 30, experiencing total internal reflection as it passes directly above and beneath the reaction volume, respectively, and exiting through the opposite edge of the cover or base. As will be explained more fully below, such light paths may be employed for detecting fluorescence using an evanescent wave measurement.

Other light paths are possible, including vertical paths passing through the cover, reaction volume and base and light paths making use of reflectance off a sample in the reaction volume, according to which light may both enter and leave the reaction volume by way of the cover 10 or base 30.

It will typically be desirable to exclude stray light from entering the reaction slide. For this purpose, any external surface of the reaction slide which is not to be used for the transmission of light may desirably be painted with an opaque paint. The choice of surfaces to be so painted will be governed by the assay to be performed and the elected methods of measurement. When any of the components 10, 20 or 30 will not be used for the transmission of light, that component may be made of a material which is itself opaque, such as metal.

When using light paths such as 40 and 41 in FIG. 4, it becomes important to transmit as much light as possible through one or both of the internal waveguides 27, keeping the losses as low as possible. It has been found that the presence of the adhesive layers 62 can cause the spacer 60 to perform like an optical fiber, the waveguides 27 corresponding to a core of an optical fiber and the adhesive layers 62 corresponding to cladding.

Figure 24:
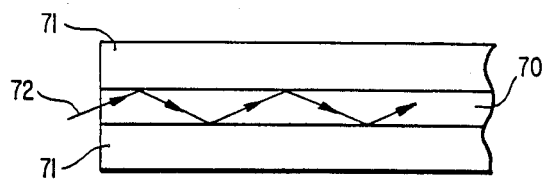
FIG. 24 schematically illustrates a vertical cross-section of a modification of a reaction slide that does not employ adhesive layers, the figure illustrating light entering that embodiment.

Refractive index mismatch between the waveguide 27 and the adhesive layers 62 produces total internal reflection of light striking the interface at angles greater than the critical angle. By way of example, reference is made to FIG. 24, wherein there are shown core 70, cladding 71 surrounding the core 70, and incident light ray 72 striking and passing through the core 70. The core 70 may correspond to the internal waveguide 27 of the overlay, and the cladding 71 may correspond to the adhesive layers 62. If, for example, the core material 70 has a refractive index $n_1$ of 1.62 and the cladding 71 has a refractive index $n_2$ of 1.52, the sine of the critical angle is $n_2/n_1$, or $1.52/1.62=0.938$. The critical angle is then 69.8 degrees.

Referring now to FIG. 7, there is shown a fragmentary vertical cross-section of a modification of the embodiment of FIGS. 1-6, the view of FIG. 7 being taken at a representative location corresponding, for example, to the extreme left-hand portion of FIG. 6. In this modification, the spacer 60 includes a second overlay 68 which is substantially identical to the overlay 20. A third adhesive layer 62 is used to join the overlay 20 and the second overlay 68. Because the second overlay 68 is identical to the first overlay 20, it forms a second pair of internal waveguides 27. The additional cross-sectional area provided by the additional waveguides 27 substantially increases the amount of light that may be introduced into the reaction volume 66 through the internal waveguides 27.

Referring now to FIG. 8, there is shown a top view of a second embodiment of a reaction slide 1 according to the current invention. The base 30 and overlay 20 of this embodiment are identical to those shown in the embodiment of FIGS. 1-6. However, the cover 10 has a length that is less than the length of the overlay 20. There is provided an end cover 75, coplanar with the cover 10 and spaced therefrom to form a gap. This gap creates vent 76, communicating the reaction volume 66 with the environment of the reaction slide 1. For the sake of clarity, the LAM assembly 50 is not shown.

Additional variations of the above-described embodiments are possible. For example, it is not necessary for a LAM assembly to be fixed on the base 30. Such an assembly may be provided separately and may be manipulated manually or using an automated system.

The adhesive layers 62 may be omitted, and an alternative method such as heat sealing may be used to join the cover 10, overlay 20 and base 30. In such a case, the spacer 60 is formed entirely by the overlay 20. Referring again to FIG. 24, in such a case the internal waveguide 27 of the overlay 20 will again act as a core 70 of an optical fiber, but the cladding 71 will be formed by the cover 10 and base 30.

Figure 9:
FIG. 9 is a top view of a cover of a third embodiment of a reaction slide according to the current invention.
Figure 10:
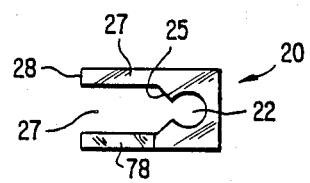
FIG. 10 is a top view of an overlay of the third embodiment.
Figure 11:
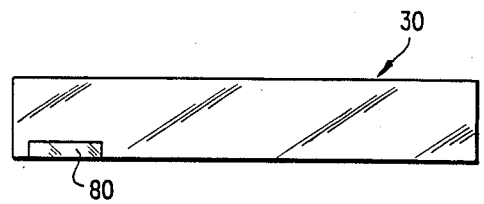
FIG. 11 is a top view of the base of the third embodiment.
Figure 12:
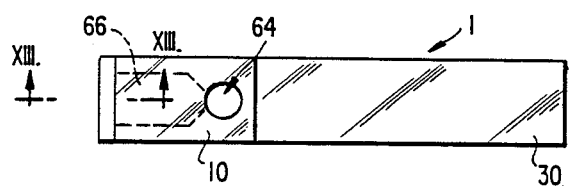
FIG. 12 is a top view of the third embodiment.

FIGS. 9-11 show top views of, respectively, a cover 10, overlay 20 and base 30 of a third embodiment of a reaction slide according to the current invention. FIG. 12 shows a top view of the assembled reaction slide of this embodiment. This embodiment differs from that of FIGS. 1-6 in the omission of conduit 26 and in that the distal end 28 of the overlay 20 is open, so that the reaction space vents longitudinally between the cover 10 and base 30 instead of vertically through the cover.

The cover 10, overlay 20 and base 30 may be secured to each other using adhesive layers 62 as described in connection with the previous embodiments, or the adhesive layers 62 may be omitted and the various elements of the reaction slide may be joined by heat sealing or solvent bonding, etc. . . . It has been found that, where heat sealing is employed, discontinuities in the heat seal often result, impairing the total internal reflection of light when passing through the waveguides 27. To compensate for such impairment, a reflective layer 78 may be placed atop the waveguide 27 of the overlay 20 through which light will be introduced. A corresponding reflective layer 80 may be placed on the base 30. Such reflecting layers also may be used in other embodiments according to the current invention, if desired.

Figure 13:
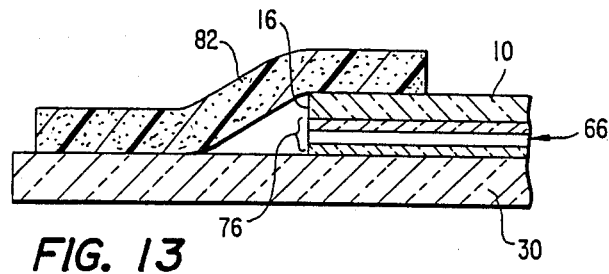
FIG. 13 is an elevational cross-section taken along line XIII—XIII of FIG. 12, further showing a liquid absorbing matrix.

FIG. 13 illustrates the open-ended reaction volume of the embodiment of FIGS. 9-12, together with the addition of a LAM 82 in a configuration preferred for use with such an open-ended reaction volume. In particular, the LAM 82 is fixed on the base 30 and overhangs the distal end 16 of the cover 10. When it is desired to remove liquid from the reaction volume 66, the LAM 82 is depressed, resulting in a localized deformation of cover 10 and LAM 82, causing contact between the LAM 82 and the fluid in the reaction volume 66 for the withdrawal of the fluid.

Figure 14:
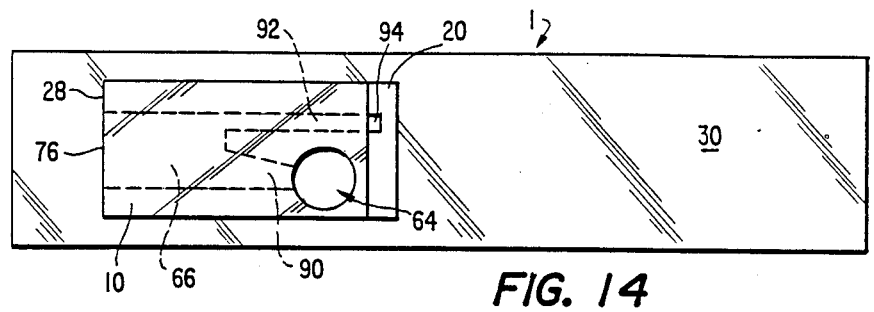
FIG. 14 is a top view of a fourth embodiment of a reaction slide according to the current invention.

Shown in FIG. 14 is a top view of a fourth embodiment of a reaction slide 1 according to the current invention. In this embodiment, the distal end 28 of the overlay is open, as is the case with the embodiment of FIGS. 9-13, such that the reaction volume 66 vents between the cover 10 and base 30. The cover 10 is shorter than the overlay 20, so that a portion of the overlay 20 may be seen extending to the right in the drawing from beneath the cover. The overlay 20 is provided with a first conduit 90 communicating the sample well 64 with the reaction volume 66 and a second conduit 92 extending backward to a point beyond the sample well, such that the end portion 94 of conduit 92 extends beyond the edge of the cover. The second conduit 92 and its end portion 94 are used for visual inspection to determine that proper filling has been achieved.

In particular, in a typical use of a reaction slide according to the current invention, that portion of the reaction slide containing the reaction volume 66 will be disposed within a measuring instrument, whereas that portion of the reaction slide containing the sample well will extend out of the measuring instrument so that a sample may be introduced into the sample well 64 when desired. When the sample passes from the sample well 64 into the reaction volume 66, it no longer is visible to the user, that portion of the reaction slide being disposed within the measuring instrument. Accordingly, when the user observes the presence of sample in end portion 94 of second conduit 92, it is assured that proper filling has been achieved. It may be seen that a reaction slide according to this embodiment is most useful in those cases when the cover 10 is opaque. In the alternative, if the cover is transparent, substantially all of the second conduit 92 may be used for visual observation of proper filling. In such a case, it is not necessary that the second conduit 92 extend beyond the end of cover 10 as illustrated, and the length of the cover 10 may be the same as the length of the overlay 20.

Second conduit 92 is not essential, as proper filling may be monitored by electro-optic means using the same light detectors used in monitoring the results of the assay being performed. Indeed, the embodiments of FIGS. 1-13 do not employ a second conduit 92.

Figure 15:
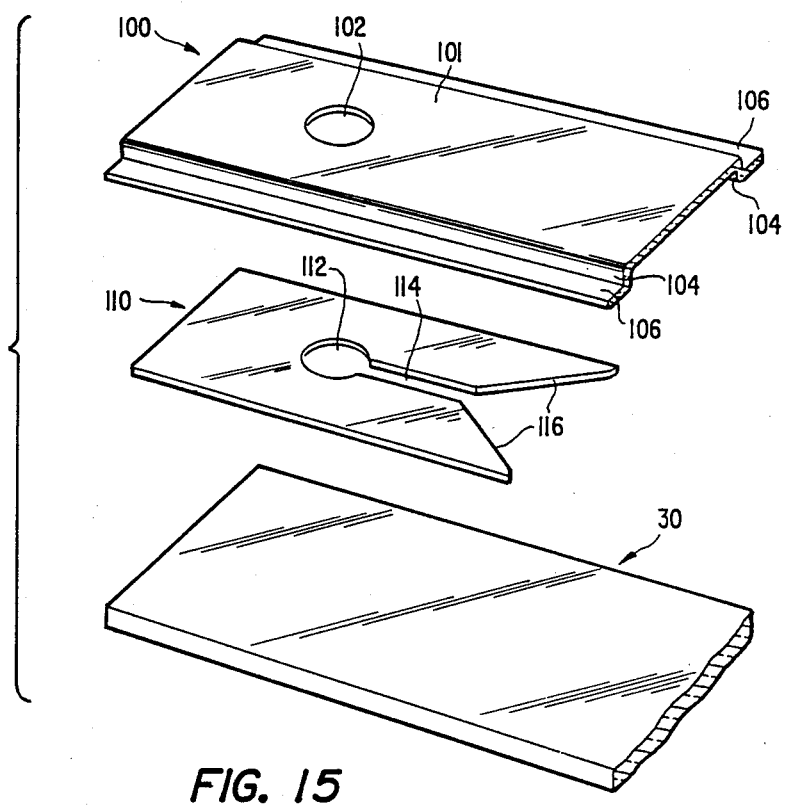
FIG. 15 is an exploded view of a fifth embodiment of a reaction slide according to the current invention.
Figure 16:
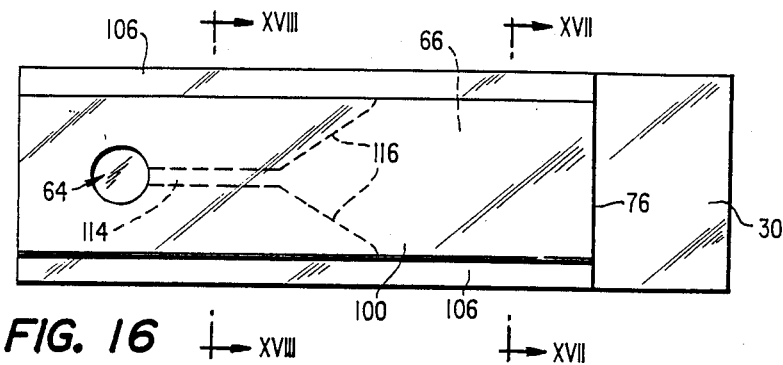
FIG. 16 is a top view of the fifth embodiment.
Figure 17:
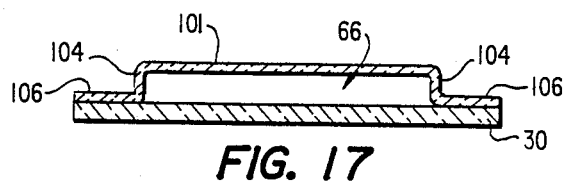
FIGS. 17 and 18, respectively, are elevational cross-sections taken on lines XVII—XVII and XVIII—XVIII of FIG. 16.
Figure 18:
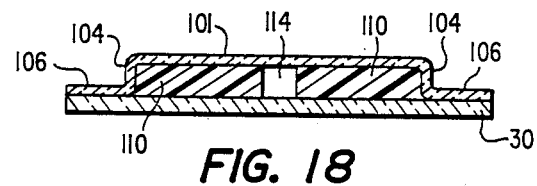

FIG. 15 is an exploded view of a fifth embodiment of a reaction slide 1 according to the current invention. A top view of this embodiment is shown in FIG. 16, with selected vertical transverse cross-sections being shown in FIGS. 17 and 18.

There is shown a base 30 on which is fixed an insert 110 and insert cover 100. Insert cover 100 is generally formed by a major planar segment 101 having a receiving opening 102, and lateral sides bent downwardly outward to form walls 104 and then laterally to form tabs 106. The tabs 106 are bonded to the base 30 with the insert 110 being disposed between the planar segment 101 of the insert cover 100 and the base 30, the height of the walls 104 generally corresponding to the height of the insert 110.

Insert 110 includes a sample receiving opening 112 communicating with a conduit 114 which ends in outwardly tapering walls 116. As the length of the insert 110 is substantially less than the length of the insert cover 100, a reaction volume 66 is formed to the right of the insert as shown in FIG. 16.

Thus, it may be seen that the walls 104 in the area of the reaction volume 66 serve the functions of the internal waveguides of the previous embodiments, and for this purpose at least those portions of the walls 104 that are disposed in the vicinity of the reaction volume 66 are made of a transparent material.

Although the insert 110 may be bonded to the base 30, variations are possible. For example, the insert and base may be formed as one piece, molded or machined to the appropriate shape and channel structure.

As will be described in more detail below, an assembled reaction slide according to the various embodiments will typically contain one or more reagents specifically selected for their utility in performing any of the many assays that may be performed using reaction slides according to the current invention. For example, liquid reagent may be placed in the reaction volume by filling through the sample well or, preferably, through the vent. The reagent can then be freeze-dried, the exact conditions of the freeze-drying process being dependent upon required optima and the type of reagent employed. There is thus produced a reaction slide, ready for use, having a premeasured amount of reagent disposed therein.

Typically, it may be desired to modify the internal surfaces of the reaction slide which will contact the sample or reagent or both to modify the liquid/solid/air contact angle of the surfaces, the surfaces thus being treated to increase their hydrophilic character. Such treatment will increase the ease with which the sample flows from the sample well to the reaction volume.

There are a variety of methods available for decreasing contact angle on a hydrophobic (or nonpolar) surface, thereby rendering it more hydrophilic. Surface active agents (or surfactants) which are typically employed as wetting agents may be used. For example, small amounts of TRITON type dispersion agents, TWEEN (polyoxyethylene derivatives of fatty acid partial esters of hexitol anhydrides) type surface active agents, and BRIJ (polyoxyethylene ethers of higher aliphatic alcohols) type wetting agents may be utilized. Surface modification via chemical derivitization of surface molecules can create polar prosthetic groups. Other techniques include surface modification using controlled electrical discharge or plasma treatment.

It should be noted that the height of the reaction volume is critical and is defined by the thickness of the spacer 60. This height should be uniform and can range from 0.001 to 0.02 inches (approximately). Typically, this height is preferably from 0.002 inches to 0.008 inches, and most preferably approximately 0.006 inches.

This order of magnitude is not only appropriate to achieve functional capillary action in the channels but is of the same order of magnitude as is required, generally, for optical waveguide transmission of light by total internal reflection. Coincidentally, this dimension is approximately of the order of magnitude required to produce preferential phase separation to the center of a flowing stream of suspended particulate or cellular material in a two phase system (or suspension) during sustained laminar flow conditions which may be achieved, as will be described below.

For construction of the reaction slide, all materials which come in contact with sample or reagent should be relatively inert. The surface properties of the materials should be such that appropriate wetting of the surface is achieved by the sample to provide proper flow conditions. Generally a low contact angle is best.

Cover 10 may be fabricated from a solid thin sheet of paramagnetic material or a laminate consisting of a coated paramagnetic material or could be fabricated from plastic or glass.

The paramagnetic material could be iron or nickel. Chemically inert thin coatings, such as polyvinyl chloride, acrylic, or polycarbonate could be utilized. A polymer with encapsulated iron oxide (e.g., magnetite) could be utilized as well.

The cover also could be fabricatd from a variety of glasses and fused quartz. Polymeric materials which could be advantageously utilized include: polycarbonate, PET (polyethylene terephthalate), PETG (glycol-modified polyethylene terephthalate), acetate, acrylonitrile, and cellulose nitrate. A variety of coextruded films, composites and polymer alloys may also be used. Of primary importance are dimensional stability, stiffness, resiliency, and optical clarity (when required). The ability of a material to be fabricated in thin sheets is also a factor. Methyl methacrylate and polystyrene are both potentially suitable materials but are difficult to fabricate in thin sheets.

The cover is typically of greater surface area (or projected area) than the reaction volume. The cover may typically assume the same length and width as the spacer (e.g., 2 inches×0.5 inches) but could be larger, if required, or smaller.

Materials which may be utilized to produce a good to excellent overlay include: polycarbonate, PETG, methyl methacrylate, polystyrene and glass. However, glass is difficult to fabricate into the required shapes. Materials which may be utilized to produce a good to moderately good overlay include: polyvinyl chloride, nylon (polyamides), PET (e.g. mylar), and acetate. Materials which may be utilized to produce an acceptable overlay include: acrylonitrile, low density polyethylene film, PP/EVA coextruded film, EVA/nylon/EVA coextruded film, PP/EVA/PE/EVA coextruded film, and oriented polypropylene film where PE=polyethylene; PP=polypropylene; and EVA=ethylene vinyl acetate. Materials which may produce an overlay of marginal acceptability include: XT (an acrylic copolymer made by Technical Plastics Extenders, Inc. of 574 Ferry St., Newark, N.J. 07105) and high density polyethylene film. In general, the better materials provide better waveguides because they have lower light scatter losses and transmit well in the visible spectrum where the most commonly employed excitation wavelengths may be found.

There are many adhesives which can be employed to secure the overlay to the cover and base. Acrylic adhesives are generally good. The best adhesives retain some flexibility, are transparent, and have low light scatter losses when cured, pressure treated, or otherwise activated. The length and width of the overlay may be varied over a wide range, but could be typically and approximately 2 inches×0.5 inches on a 3 inch×0.75 inch base. Thickness of the spacer is typically in the range of 0.002 to 0.010 inches. Thinner spacers may occasionally result in impeded capillary channel flow. Thicker spacers tend to lose liquid at the air interface adjacent to the edge of the reaction volume due to poor capillary action at larger diameter conduits.

The base is a solid support and can be made from a variety of materials. It should be rigid enough to maintain and support the reaction volume geometry, transparent in the reaction volume region (if required for monitoring) and capable of being bonded to the spacer/cover component. Fluorinated hydrocarbons such as Teflon make poor bases because they are difficult to bond. Glass is an acceptable material. Excellent bonding may be achieved with polycarbonate or methyl methacrylate base materials. A typical minimum thickness for the base is approximately 0.020 inches for a material such as polycarbonate. An aluminum base (if transparency is not required) could be thinner. If the base is too thin, it may bend too easily and alter the volume of the reaction volume unintentionally during handling or manipulation during an assay. If the base is too thick, it may take too long to achieve thermal equilibrium for a temperature controlled assay. This is especially true for materials with low heat conductivities. The length and width of the base are variable. The base could be as small as 0.25 inches in width and 1 inch in length (or even smaller). Typically, the base will be approximately 0.75 inches in width and 3 inches in length. This provides enough room for a sample well, connecting conduit, and reaction volume with vented end. There would also be an area to grip the slide with thumb and forefinger for handling and placement and another area for an optically or magnetically readable code to provide information to the analytical instrument employed. This information might include the type of assay, control parameters, calibration information for that batch of reagent, etc. As will be described later, the base could be wider (or longer) if multiple assays are to be performed on the same sample. In such a case, multiple reaction spaces might be used in parallel (or series) communication with the sample well. The base could consist of a composite material (e.g., two layers, such as a lower layer of aluminum, iron, or other metal with a hole under the reaction volume. Atop this layer and affixed thereto would be an upper layer of transparent material, such as polycarbonate, which would define the bottom of the reaction volume to allow light transmission through the hole in the lower layer.

When used, the reflective layer (78, 80 FIGS. 10, 11) can be made by applying a thick film of aluminum paint. Other methods include chemical deposition of silver metal and vacuum vapor deposition of silver or aluminum. Another fabrication technique is to employ metallized heat sealable film, for example, metallized linear low density polyethylene (LDPE) film of approximately 20 microns thickness (or less). Other metallized polymer films may also be utilized if coated with a heat sealable material such as polyvinylidene chloride. An example is metallized heat sealable polypropylene film (polypropylene coextruded with heat sealable materials). Other possibilities include metallized cellophane coated with a heat sealable material. Metallized films may be heat sealed or glued with an adhesive (e.g. cyanoacrylates) to the base and cover of the reaction slide. Metallized glass may also be utilized.

As stated above, a currently preferred method of use of a reaction slide according to the current invention involves the use of one or more sources of light external to the reaction slide and one or more light detectors external to the reaction slide. Illustrative examples of such instrumentation and use will now be described.

Figure 19:
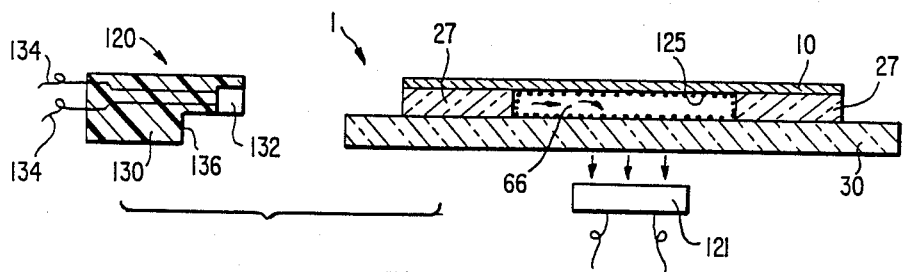
FIG. 19 shows a transverse cross-sectional elevation of a reaction slide, a preferred embodiment of a light source, also in section, and a light detector, the light source and light detector being disposed for making a reflectance measurement.

Shown in FIG. 19 are a transverse vertical cross-section of a preferred embodiment of an external light source 120, a transverse vertical cross-section of a representative embodiment of a reaction slide 1, the cross-section being taken in the region of the reaction volume 66, and a light detector 121 disposed beneath the reaction slide 1 in the area of the reaction volume 66. A dried reagent 125 is deposited on the walls of the reaction volume 66.

In this embodiment, the light source 120 comprises a plastic housing 130 supporting an LED 132 having electric leads 134. As shown, a step 136 is formed in housing 130. As shown, the cover 10 may be made of an opaque material such as a metal.

In use, the light source 120 and reaction slide 1 will mate such that the step 136 receives the base 30 of the reacion slide and the LED 132 is disposed above the base 30 and in contact with or closely adjacent an internal waveguide 27 of the reaction slide.

Figure 20:
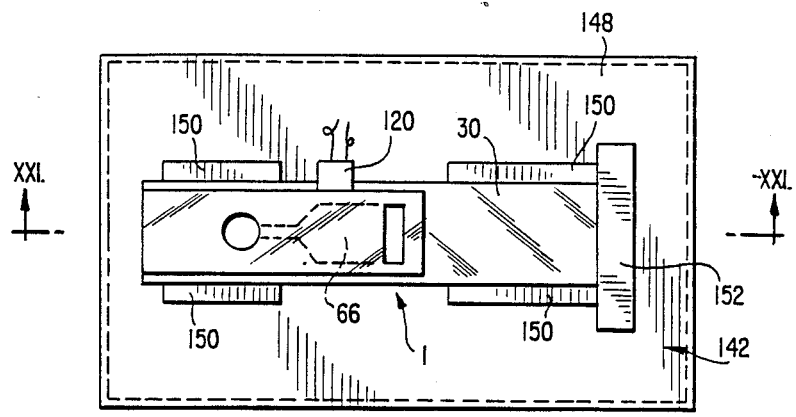
FIG. 20 is a top view of a reaction slide disposed in a housing for making a reflectance measurement, a cover of the housing being removed.
Figure 21:
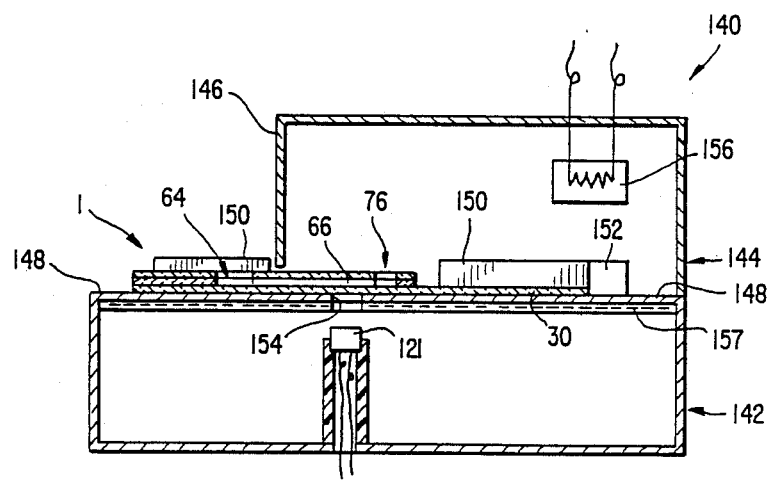
FIG. 21 is an elevational cross-section taken on line XXI—XXI of FIG. 20, also showing the cover of the housing.

The arrangement illustrated in FIG. 19 is designed to employ a light path such as that shown at 41 in FIG. 4. A more detailed example of instrumentation for accomplishing such measurement is shown in FIGS. 20 and 21. Housing 140 comprises lower housing 142 and cover 144 resting on or integral with lower housing 142. A lower end of wall 146 of cover 144 is spaced from the top 148 of lower housing 142 by a distance which is sufficient to allow the reaction slide 1 to be inserted. Lateral guides 150 and stop 152 establish a proper position of reaction slide 1 for a measurement. Light source 120 and light detector 121 are disposed within the housing 140, as shown. There is provided in the top 148 of the lower housing an opening 154, disposed immediately beneath the reaction volume of the reaction slide such that light passing through the base 30 of the reaction slide may reach the light detector 121.

Sample well 64 of reaction slide 1 is disposed outside the housing 140, such that the reaction slide 1 may be inserted into the housing 140 before a reaction is initiated.

The light detector 121 may be used to monitor the progress of sample entry into the reaction volume 66 and the subsequent progress of the reaction within the reaction volume 66. The light source 120, reaction volume 66 and light detector 121 are disposed in a portion of the instrument that is isolated from ambient light. Desirably, those portions of the reaction slide 1 which are exposed to ambient light are made of opaque materials or are painted so as to aid in the exclusion of stray light from the reaction volume 66.

Temperature control is provided for the reaction slide by means of heaters of a thermal control system, illustrated schematically as element 156. One form of such a heater may be a conductive heater strip 157 fastened to the bottom of plate 148. Regardless of the form of thermal control system used, it is desirable that it be capable at least of maintaining the temperature of the plate 148 at 37° C.

The instrument shown in FIGS. 20 and 21 is not of a standard commercially-available type but is instead custom designed for use with reaction slides. As in the case of other instruments currently available for decentralized testing, optical or magnetic code reading capability is preferably present to provide for identification of the assay to be performed and of the particular reaction slide being used, along with calibration information. Such a code may be affixed to the reaction slide during manufacture. In addition, other structure may be present to provide for mixing when required (to be described below). As also described below, there will desirably be associated with the illustrated instrumentation a system microprocessor, display or other data presentation means, any necessary analog-to-digital converters, power supplies, and the like.

As may be seen from a consideration of FIG. 21, it is desirable for the spacing between the lower end of wall 146 and the plate 148 to be as low as possible to aid in the exclusion of ambient light. Accordingly, this embodiment of instrumentation is not conducive to the use of a reaction slide that is provided with a LAM assembly 50 as shown in FIG. 6. Therefore, there may be provided within the housing 140 a movable structure for advancing and withdrawing a separate LAM from the vent 76.

One type of assay that may advantageously be conducted using the apparatus illustrated in FIGS. 20 and 21 is a measuremnt of prothrombin time. Illustrative results of such a measurement will now be described with reference to FIG. 22.

Figure 22:
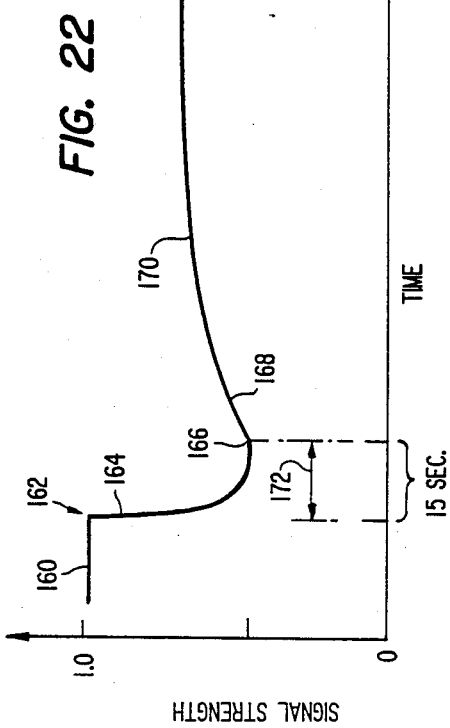
FIG. 22 is an exemplary graph showing typical results of a measurement of prothrombin time.

FIG. 22 shows a resulting light scatter curve obtained when a plasma sample is deposited in the sample well 64 of a reaction slide containing dried thromboplastin calcium reagent. This curve is unexpected and quite different from the 90° light scatter signal observed for the same assay using liquid reagents. The same type of photodetector was employed in earlier work with liquid reagents. See for example Oberhardt, B. J., *Monitoring System for Fully-Automated Prothrombin Time Determination*, Digest of the 7th International Conference on Medical and Biological Engineering, Stockholm, Sweden, 1967, p. 187, which is hereby incorporated herein by reference. With liquid reagents, however, different and considerably less informative curves result. An apparatus using the same photodetector as in the present invention and which employed liquid reagents to produce the previously published curves is disclosed in U.S. Pat. No. 3,450,501. This patent is hereby incorporated herein by reference.

In prothrombin time determinations that are performed with liquid reagents and plasma samples, the scatter intensity curve starts off low, increases upon addition of reagent, and increases further at the formation of the gel clot.

The different result obtained with dried reagent may possibly be explained as follows, although the present invention is by no means to be construed to be limited by the following explanation which is simply given to illustrate one current plausible explanation of the results obtained with the present invention. In accordance with the illustration of FIG. 22, the sample rapidly propagates through the conduit 26 and into the reaction volume 66. The liquid front advances swiftly, filling the reaction volume, solubilizing the reagent 125 and initiating the coagulation reaction. The light intensity (FIG.

22) as detected by the photodetector 121 is initially high at the level indicated at 160. This is presumed to be because the dried reagent is highly refractile. Upon addition of sample at a particular point in time, 162, the light intensity drops precipitously as shown at 164 due to dissolution of the reagent, which apparently provides an improved refractive index match. Elimination of air as the sample moves into the reaction space probably contributes significantly to matching of refractive indices. The decreasing scatter curve may then level off before the beginning 166 of a discernable rise 168 is observed. This rise may be due to the increase in scattered light intensity arising from the polymerizing system which at or near this point in time has formed a gel clot. The scatter intensity continues to increase more slowly, 170, eventually levelling-off.

The prothrombin time is equal to or highly correlated with the time elapsed between sample addition 162 and the clot formation endpoint 166. Prothrombin time (interval 172) is shown below the abscissa as 15 seconds (for the particular assay illustrated). It is believed that this is the first successful example of a prothrombin time determination being performed via light scatter measurements with dry reagent.

Figure 23:
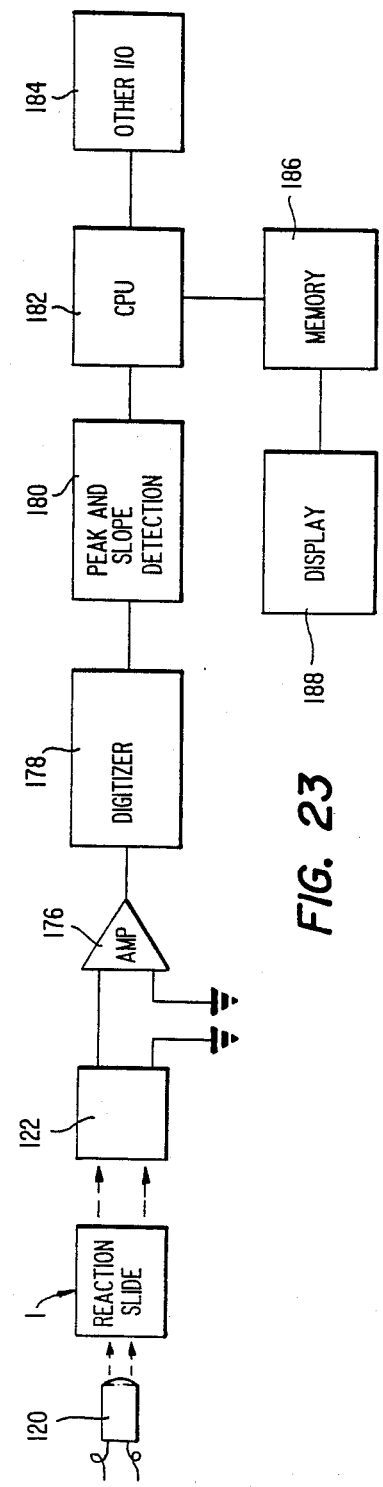
FIG. 23 schematically illustrates apparatus for measuring prothrombin time.

FIG. 23 shows a simplified systems block diagram of how the analog signal in FIG. 22 may be interpreted. The light source 120 transmits light through the reaction slide 1. Light scatter at 90° is monitored by the photodetector 122 and amplified at 176. Digitizing is accomplished at 178, and peak and slope detection are accomplished in block 180. At 180 start time and endpoint detection are determined, as well as kinetic curve characteristics. The resultant digital information is sent to the microprocessor CPU, 182, which has other inputs and outputs 184. Block 186 contains data and program memories. The results are read on the display 188. In addition to monitoring the assay kinetics, the dynamics of sample entry into the reaction space and initial interaction with the reagent are monitored, as well, as a consequence of the geometry and structure of the reaction slide. The initial fall of the curve therefore provides information for quality control of proper sample addition.

Figure 75:
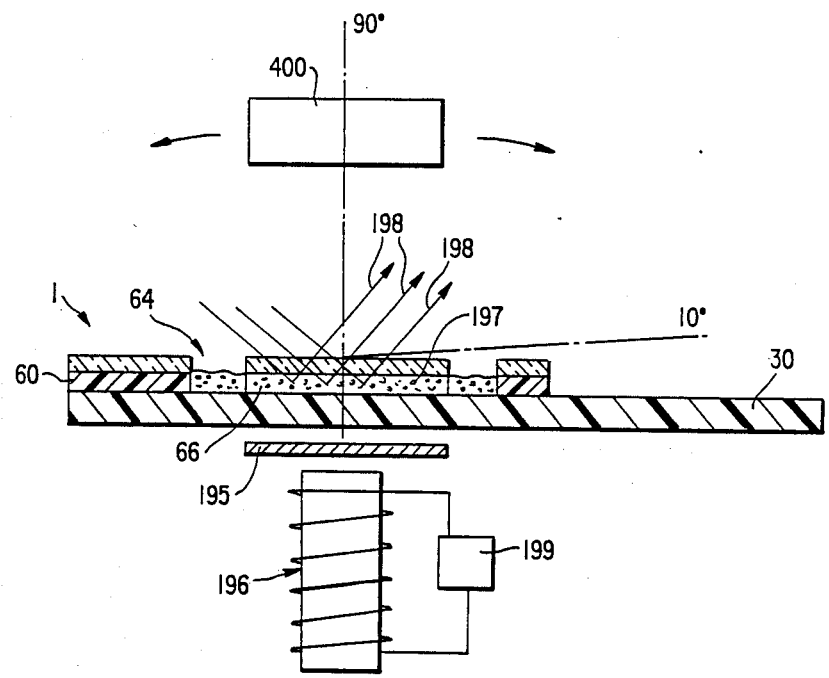
FIG. 75 is a longitudinal vertical cross-section of a reaction slide together with apparatus for using suspended magnetic particles to measure a coagulation reaction.

The above is an example of a measurement made by light scattering. There will now be described an example of a measurement made by reflectance. In this particular example, changes in reflectance are used to monitor viscosity changes during a coagulation reaction. Shown in FIG. 75 is a reaction slide 1 disposed above and in close proximity to a permanent magnet 195. Beneath the permanent magnet 195 is an electromagnet 196 which is driven by a power supply 199 for cycling voltage on and off at a desired frequency. There is also provided a light source for providing incident light and a detector positioned for detecting light rays reflected from the sample within the reaction volume 66.

The reflected rays illustrated as rays 198 are detected by a detector 400. Detector 400 can be positioned at any position between the 90° and the 10° positions, inclusively, shown in FIG. 75. Preferably detector 400 can be positioned between 90° and 45°, most preferably between 90° and 75°. A measurement that has successfully been conducted with such apparatus will now be described.

The reaction slide was prepared in advance by forming a slurry of a coagulation reagent and inert magnetic particles suspended in the reagent. The coagulation reagent was thromboplastin-calcium, and the magnetic particles were magnetite. Inert magnetic particles work well when provided in the range from approximately 5 to 50 milligrams per milliliter of liquid reagent. The slurry was applied to the reaction slide and freeze dried.

To perform the assay, the reaction slide 1 was introduced to the apparatus in position as shown in FIG. 75. The light source was a light emitting diode, and the detector was a silicon photodiode. A chart recorder was AC-coupled to a photodiode amplifier. The permanent magnet 195 was in the form of a sheet (which may be made of a flexible or rigid magnetic material). The power to the electromagnet was cycled at a frequency of 1 Hertz. A sample of blood plasma was introduced into the sample well 64 and filled the reaction volume 66 solubilizing the dry reagent, resuspending the magnetic particles as shown at 197, and initiating the coagulation reaction. The permanent magnet 195 causes the magnetic particles to be drawn downwardly and lie down against the base 30 in an orientation parallel to the plane of the permanent magnet. However, each cycle of energy supplied to the electromagnet 196 causes the magnetic particles to stand upright like tiny whiskers in an orientation of alignment along vertical field lines. At the end of each such energy cycle, the particles lie flat again.

The detected reflected light 198 shows a time-varying pattern of light intensity in accordance with the above-recited changes in orientation of the magnetic particles. The light intensity is less when the particles lie flat than when they stand upright.

The detected light intensity shows an initial peak at sample addition. Thereafter, the detected light intensity cycles between maximum and minimum values in accordance with the frequency of the cycling of the electromagnet 196. During the period before clot formation, the difference between the maximum and minimum values of the detected light intensity increases. However, the peak-to-peak light intensity oscillations begin to fall off from their maximum values when a clot has started to form. At this point, the endpoint has been reached. In the case of prothrombin, the elapsed time between the sample addition peak and clot formation or clot onset (endpoint) is easily measured. Resolution may be increased by increasing the oscillation frequency.

For determining prothrombin time, the above-described approach works extremely well using whole blood as well as plasma. It is expected to work well for other types of blood coagulation assays. The measurement may be made using transmitted light instead of the described method of using reflected light. However, it is thought less convenient to use transmitted light than reflected light.

The above provides one example of a light scattering measurement followed by one example of a light reflecting measurement. Alternative means for introducing light into the reaction volume 66 for such measurements will now be discussed together with a discussion of other types of optical measurements. In particular, there will be discussed optical measurements based on transmission/absorbance, chemiluminescence, reflectance, fluorescence, and combinations of these techniques.

Figure 25:
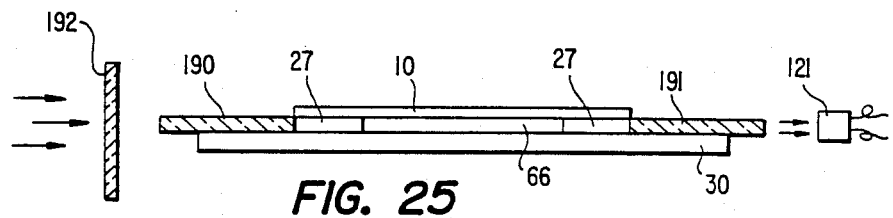
FIG. 25 illustrates the use of a reaction slide (unsectioned), external waveguides and apparatus for making a transmission/absorbance measurement.

Transmission/absorbance, or optical density measurements, involve measurement of the ratio of light intensity before and after light passes through a sample in the absence of (or excluding) scattering. The Beer-Lambert Law describes the phenomenon. Standard detectors are employed in a "line of sight" configuration with the light source, as shown in FIG. 25. Incandescent or LED light sources may be used.

FIG. 25 also illustrates an alternative means of introducing light into the reaction slide and of measuring light that has left the reaction slide. In particular, there are provided two external waveguides 190, 191 which respectively carry incident light to one of the internal waveguides 27 of the reaction slide 1 and receive light that has been passed through the other internal waveguide 27 and channel the received light to the photodetector 121. The external waveguides 190, 191 may be made of the same types of materials used to produce the overlay 20 of a reaction slide, as described above. Accordingly, it may be seen that use of an external waveguide or waveguides 190, 191 provides structure for introducing light into the reaction slide 1 that is alternative to the polymeric housing 130 illustrated in FIG. 19.

An optical filter 192 may be used for wavelength selection.

In FIG. 25, colorimetric or turbidometric measurement is achieved. Light rays pass through filter 192, travel through external waveguide 190 and through an internal waveguide 27, then illuminate reaction volume 66. They pass through the reaction volume, through the internal waveguide 27 at the right, and are transmitted through optional second external waveguide 191. The light rays are then directed to an appropriate detector 121.

Figure 26:
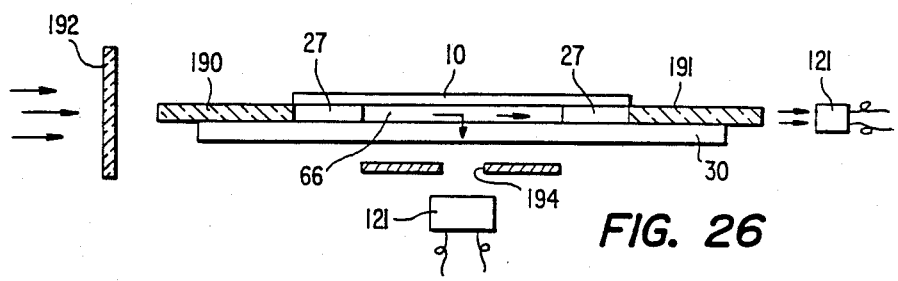
FIG. 26 is a view similar to that of FIG. 25, illustrating simultaneous measurements of light scattering and transmission/absorbance.

In FIG. 26, a second light detector 121 for detecting scattered light and an aperture 194 to restrict detection to light scattered at or near 90° have been added to the arrangement of FIG. 25. Aperture 194 is analogous to aperture 154 of FIG. 22. FIG. 26 therefore illustrates an embodiment which allows simultaneous detection of scatter and absorption. It is based upon a combination of light paths 40 and 41 in FIG. 4. This monitoring strategy may be useful during the formation of precipitates or large polymers with characteristic absorption spectra.

Figure 27:
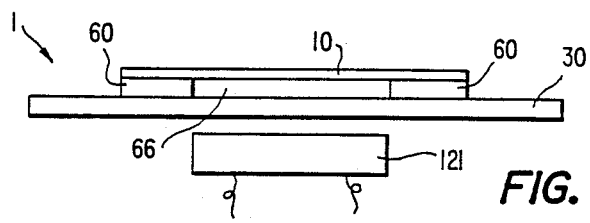
FIG. 27 illustrates a reaction slide and a light detector, disposed for making a measurement based upon chemiluminescence.

FIG. 27 shows an embodiment employing a reaction slide 1 with a transparent base and detector 121, but no light source other than that initiated by a chemiluminescent reaction taking place within the reaction space. The chemiluminescent reaction can be triggered upon the addition of sample.

Figure 28:
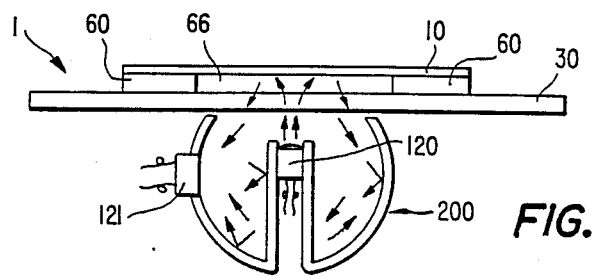
FIG. 28 shows a reaction slide disposed above a partial integrating sphere for making a measurement based on reflectance.

FIG. 28 shows an embodiment based upon reflectance. A partial integrating sphere 200 mounts a light source 120 and a light detector 121. The partial integrating sphere is positioned beneath the base 30 of a reaction slide 1 having a reaction volume 66 and cover 10. Rays reflected back into the partial integrating sphere from within the reaction slide are detected to allow measurement of the reaction. It should be noted that the spacer 60 is not employed to provide internal waveguides for transmission. Internal waveguides are not necessary for the type of measurement performed in FIG. 27, either, but they can of course be used, if desired, by positioning a detector so as to intercept light exiting through an internal waveguide.

More generally, such reflectance measurements capture light reflected in any desired direction from surfaces or surface layers. A photodiode or photoconductive cell may be used along with a filter for wavelength specificity. The Kubelka-Monk Theory is a useful model for reflecting systems.

A further method of detection may be based upon fluorescence and involve the use of materials which are fluorescent and hence absorb ultraviolet light and emit light of a longer wavelength, frequently in the visible range. Fluorometry may be used in a reflective mode, similar to photodensitometry, for example to quantitate samples on chromatograms. Variations are possible, together with the use of fluorescence in combination with other modes of detection. For example, a detector may be placed at a fixed angle, typically 90°, from the direction of transmission through a sample, as in nephelometry. As will now be described in connection with FIGS. 29 and 30, fluorescence also may be detected using an evanescent wave, for example at a solid/liquid interface. Light paths such as those shown at 42 and 43 in FIG. 4 may be used.

Figure 29:
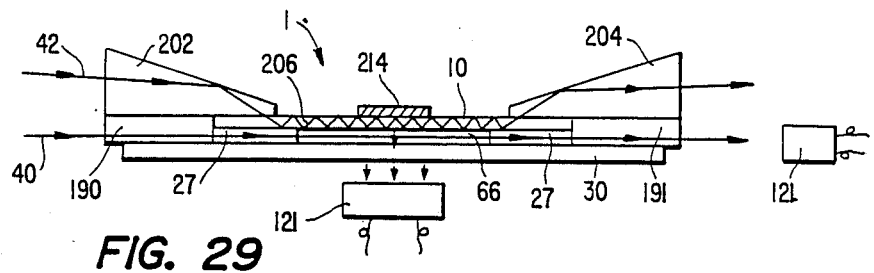
FIG. 29 illustrates simultaneous measurements based on light scattering and transmission/absorbance through the reaction space and the use of the cover in making a fluorescent evanescent wave measurement.

FIG. 29 illustrates how a reaction slide 1 may be used to perform fluorescent evanescent wave measurements near a wall (cover/liquid interface) and alternating with or simultaneous with colorimetric (or fluorescent) measurements through the reaction volume 66. A first prism 202, which typically is not part of the reaction slide but rests on top of the cover 10, is affixed to and mechanically supported by first external waveguide 190 which, in turn, rests atop the base 30 of the reaction slide 1. Fluorescent light rays 42 are refracted by prism 202 and emerge, entering the cover 10 at an angle somewhat greater than the critical angle. The rays 42 undergo total internal reflection within the cover 10, as shown at 206, and produce intense evanscent waves at the interface between the cover 10 and the liquid in the reaction volume 66. The evanescent waves excite fluorescent molecules bound at or near the wall as a result of selective binding (or depletion) associated with an assay. The total internal reflected light then passes out of the cover and is removed by second prism 204 situated atop second external waveguide 191, passing out of the system. Fluorescent emission of light is detected by a detector 121 positioned beneath the transparent base of the reaction slide.

Light ray 40 is sent into the system through external waveguide 190 and internal waveguide 27, to illuminate the reaction volume 66. It emerges through the opposite internal waveguide 27 and second external waveguide 191, exiting to be detected by a detector 121 positioned laterally of the reaction slide.

Illumination rays 40 and 42 would typically be of the same or similar wavelength but could excite molecules with different emission spectra. In this figure, the detector 121 disposed beneath the base 30 is shown to detect fluorescence emission resulting from either excitation ray. Twin detectors could be utilized, as well. Convection currents are created within the reaction volume 66, using any technique to be described later.

The arrangement in FIG. 29 allows monitoring of the progress of complex reactions involving bulk liquid species undergoing reactions and simultaneous receptor site interactions at the wall.

Figure 30:
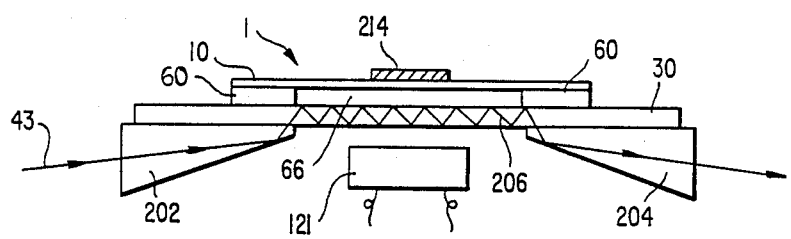
FIG. 30 illustrates the use of the base of a reaction slide in making a fluorescent evanescent wave measurement.

FIG. 30 shows another arrangement using evanescent wave fluorescent detection. One application of this arrangement is rapid measurement of hematocrit in a blood sample. In this case, prisms 202 and 204 rest beneath the base 30 of the reaction slide to produce total internally reflected light 206 from the initial ray 43. Spacer 60 is not used in this example to transmit light. A detector 121 is positioned beneath the base 30 opposite reaction volume 66. A highly soluble fluorescent dye is reversibly absorbed to the cover wall or base inside the reaction volume. The dye may also be contained in a highly porous space-filling soluble hydrophilic polymer with capillary or interstitial structure. The fluorescent dye is chosen such that it neither enters nor adheres to the blood cells and is compatible with the blood plasma. In general, most fluorescent dyes with net negative charge in solution will be suitable, since they will not bind to or adsorb to the surfaces of red blood cells and platelets (which have negative surface charge). The exceptions are dyes that can enter the red cells. These exceptions may generally be rendered suitable by covalent bonding to an appropriate larger molecule (e.g. dextran or polyglycols).

When the blood sample enters the reaction volume 66, the dye is rapidly dissolved in the plasma, the rapidity of dissolution being aided by the flow dynamics through the tortuous paths in the space filling soluble polymer and/or by electromechanical mixing effect, to be described below. The fluorescent signal near the wall therefore quickly approaches a steady state, indicative of the concentration of fluorophore in the plasma. From this concentration, the known volume of the dye (and polymer, if employed) and the volume of the reaction volume, the plasma volume and hematocrit can be readily calculated.

Fluorescent dyes which may be possible candidates for use in the hematocrit determination application may include: rhodamine B, berberine sulfate, ethidium bromide, methylene blue, thionine, and others, such as cyanine dyes (e.g., 3,3'-diethyloxadicarbocyanine).

The method of hematocrit determination by dye dilution is old (Eric Ponder, *Hemolysis and Related Phenomena*, Grune & Stratton, New York, 1948, pp. 51–53). It has been applied in various forms, such as in a continuous flow analyzer (Oberhardt, B. J. and Olich, J., U.S. Pat. No. 4,097,237). Recently the method has been applied using evanescent wave fluorescence in a capillary tube (Block, M. J. and Hirschfeld, T. B., European Patent Application, Publication No. 0128723; Application No. 84303759.9; filed June 5, 1984; published Dec. 19, 1984).

The present invention is an improvement in that it utilizes a self-contained convective effect to rapidly dissolve or aid in dissolving the dye, thereby yielding more rapid test results than would be otherwise possible. Additional improvement is afforded in terms of increase in the accuracy of the determination in the laterally flowing system created by forced convection, to be described more fully below. In this flowing system, when lateral flow is alternatively established, blood cells (particularly erythrocytes) will on the average tend to rise to the center of the stream due to hydrodynamic lift forces. This removal of cells from the excitation region of the evanescent wave, however brief, provides an interval for eliminating cell interference artifacts in the fluorescence measurement.

Various exemplary methods for inducing forced convection currents within the reaction volume 66 of a reaction slide 1 will now be described with reference to FIGS. 31–34. Such forced convection currents promote rapid and thorough mixing.

Figure 31:
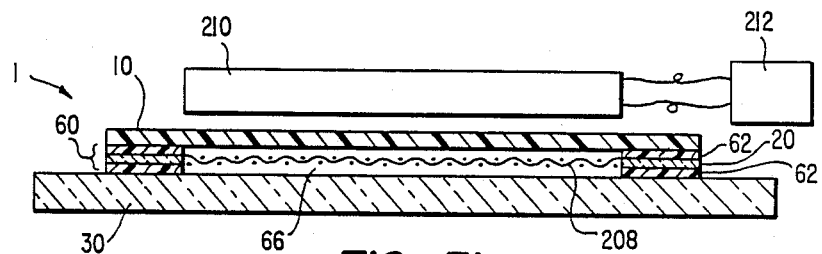
FIG. 31 illustrates the use of a screen for setting up convective currents in the reaction space.

In FIG. 31 is shown a fine paramagnetic mesh or screen 208 disposed within the reaction space. The screen 208 may be supported by sandwiching it between the cover 10 and base 30. In the embodiment shown, the lateral edges of the screen are pressed against an overlay 20 by an upper adhesive layer. The mesh 208 must be capable of undergoing translational movement or bending while being confined within the reaction volume 66.

The mesh may be a metallized polyester screen having a coating, for example, of nickel. Other embodiments are possible. For example, the screen may be made of nylon or polyester, coated with a dispersion containing magnetic iron oxide. In the alternative, the screen itself may be made of iron or steel and may be coated with a protective plastic coat such as an elastomeric coating. As an alternative to a mesh, a solid flexible support may be used, with a distributed array of magnetic particles such as magnetite coated with inert polymer bound to the solid support.

An oscillating magnetic field is supplied by electromagnet 210 connected to an appropriate time-varying electrical power source 212. Under the influence of this magnetic field, the mesh undergoes mechanical oscillations which translate to the development of continuous oscillatory flow in the liquid contained within the reaction volume for as long as the driving signal is applied. The induced flow can be used to: (i) maintain a steady state level of convection in a reaction volume containing sample and reagents; (ii) assist in rapidly dissolving a reagent; or (iii) increase convection near the wall (cover or base) to facilitate transport of species to bound reagents.

Figure 32:
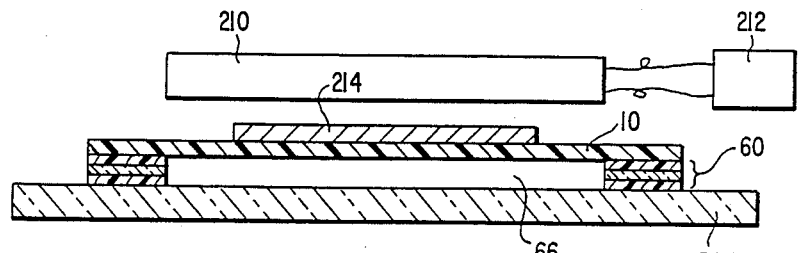
FIG. 32 illustrates the use of a permanent magnet for setting up convective currents in the reaction space.

FIG. 32 shows an alternative arrangement for mixing. In this figure, permanent magnet 214 is affixed to cover 10 and driven into an up/down oscillation by electromagnet 210 supplied by an electrical driving signal from 212. The cover 10 moves along with the magnet 214 as essentially one unit, causing periodic alterations in the volume of the reaction volume 66. The inflow and outflow of liquid produces mixing. The mixing resulting here is well suited for moving liquid in the vicinity of the cover/liquid interface. To achieve this type of mixing, the cover 10 may be fabricated from a thin paramagnetic material, obviating the need for a separate magnet 214. If a separate magnet is used, it may be doughnut shaped, or disc shaped. It may also be made of flexible ceramic magnetic material. A similar arrangement also is illustrated in FIGS. 29 and 30.

Figure 33:
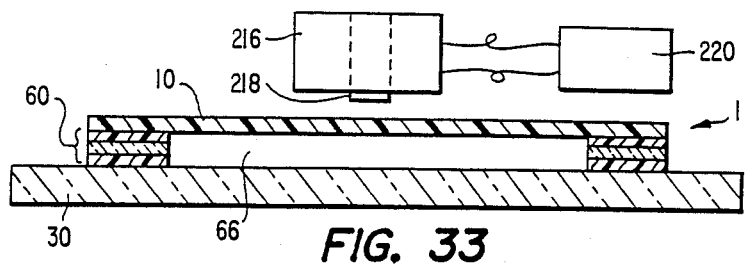
FIG. 33 illustrates the use of a solenoid for setting up convective currents within the reaction space.

FIG. 33 shows an arrangement which provides yet another alternative for producing and sustaining a controlled convection within the reaction volume 66. In this case, a solenoid 216 is employed, having a rod 218 and a coil which is driven by an appropriate intermittent unidirectional or time varying current source 220 to push rod 218 against and deflect the cover 10. The solenoid may be spring-loaded to retract the rod upward after cessation of the current.

Figure 34:
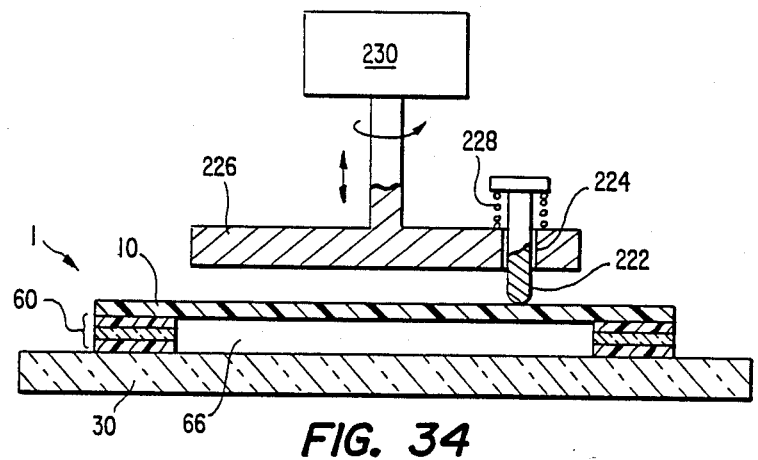
FIG. 34 illustrates apparatus for producing localized deflection of the cover to produce convective currents within the reaction space.

In the alternative and as shown in FIG. 34, there may be provided a projecting element 222 passing through a hole 224 in an orbiting disk 226. Tension spring 228 biases projecting element 222 downwardly as shown in the drawing. Drive 230 initially moves disk 226 downwardly for contact between the projecting element 222 and the cover 10 of a reaction slide. At such time, projecting element 222 pushes against cover 10 at a localized pressure point with a force, the magnitude of which is governed by spring 228. Thereafter, drive 230 rotates disk 226 about the axis thereof, causing the localized pressure point to trace a circle on the upper surface of the cover 10. The cover 10 accordingly experiences a localized deflection that moves in a circular pattern, following the position of the projecting element 222. Such localized deflection of the cover 10 causes mixing in the reaction volume 66. It has been found that a deflection of 0.005 inches may be produced in a polycarbonate cover 10 by a force of 3 ozs., applied with a projecting element 222 having a 0.100 diameter circular cross-section and a rounded bottom.

Yet another approach to mixing (not shown) is to utilize a cover fabricated from a piezoelectric material or containing a piezoelectric material affixed thereto. In this case, motion of the cover would be produced piezoelectrically by application of the appropriate voltage.

As noted above, a reaction slide according to the current invention may be used to conduct assays in which the results are measured using non-photometric techniques. That is, in addition to transduction of light energy (e.g., transducers of the photoconductive, photodiode or photomultiplier type), the reactinn slide may employ other mechanisms for energy conversion. Additional types of transducers that are applicable to a reaction slide according to the current invention include calorimetric transducers, electrochemical transducers and viscosity transducers. Examples of these will be described with reference to FIGS. 35–37.

Figure 35:
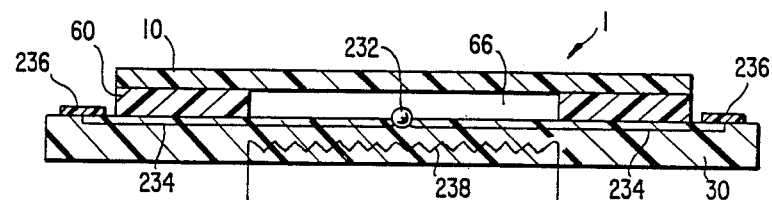
FIG. 35 is a transverse elevational cross-section of a reaction slide provided with a calorimetric transducer.

Shown in FIG. 35 is a transverse vertical cross-section of a representative embodiment of a reaction slide according to the current invention. Calorimetric transducer 232 such as a thermistor, thermocouple or thermopile is mounted by the base 30 of the reaction slide such that at least a portion of the transducer 232 is directly exposed to the reaction volume 66. Electric leads 234, embedded in the base 30, extend from the transducer 232 to electric contacts 236 mounted on the base 30 in a known manner. For example, electric contacts 236 may be a conventional thick-film polymer having contained therein a conductive powder. Appropriate instrumentation is attached to the electric contacts 236.

The calorimetric transducer 232 may be used to measure temperature change or heat input or output in an isothermal system. Thus, the heat generated during a chemical reaction may be monitored and used to quantify analyte concentration using information related to heat of reaction.

As explained in more detail below, a reaction slide according to the current invention may be configured to allow liquid to enter and exit the reaction volume 66 at predetermined times. In such a case, using a calorimetric transducer 232, temperature may be measured before and after residence of the sample in the reaction volume. During residence, a known amount of heat may be transferred to the liquid, as by a resistive heater 238 in the base 30 of the reaction slide. From the temperature change (before and after heat input) the specific heat capacity of the liquid (and analyte concentration for a pure dissolved analyte and moderate concentration) may be measured using well-established procedures.

Figure 36:
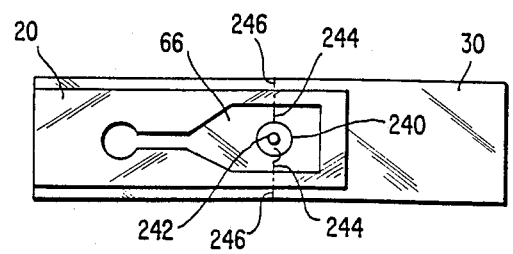
FIG. 36 is a top view of a reaction slide, with the cover removed, the reaction slide being provided with an electrochemical transducer.

The use of electrochemical transducers will now be described with reference to FIG. 36, which is a top view of a reaction slide according to the current invention with the cover removed. First and second electrodes 240, 242 are provided in the reactinn volume 66 and are spaced from each other. In the embodiment shown, the electrodes 240 and 242 are conductive circular regions deposited on the base 30 using known techniques. An electric lead 244 extends from each electrode to electric contacts 246 formed on the base 30 of the reaction slide, taking care that the lead from the inner electrode 242 does not make contact with the outer electrode 240.

Such electrochemical transducers may be of the potentiometric type (e.g., pH measuring electrodes). In such a case, a voltage may be generated which is proportional to the analyte species concentration.

Also, amperometric methods may be employed, for example using vacuum vapor deposited gold and silver. A polarographic system may be used, which is a current measuring system having two or three electrodes, such as a reference electrode, working electrode and measurement electrode. An example is an amperometric potentiostat. Such a system may be used with the application of various voltammetric sweep patterns, depending upon the analyte species to be detected.

Conductivity methods also may be applied. In such a case, an electrode in the presence of an analyte exhibits a change in conductance or resistance. Examples of this type include electrodes fabricated from low dimensional materials such as polyacetylene, polypyrrole, and the like.

Enzyme electrode systems and antibody electrode systems also may be used.

Figure 37:
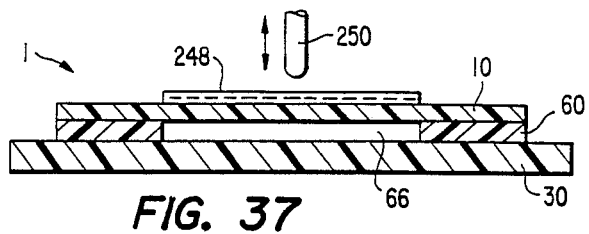
FIG. 37 is a transverse cross-sectional elevation of a reaction slide provided with a viscosity transducer.

FIG. 37 illustrates the use of a viscosity transducer. There is shown a strain gage 248 mounted on the cover 10 of a reaction slide 1. Using the strain gage 248, the rate of bending or movement of the cover 10 or, in the alternative, the rate of recovery from a downward push imparted by a solenoid-actuated push rod 250 may be measured. Changes in the viscosity of fluid in the reaction volume 66, such as occur in coagulation reactions within the reaction space, may therefore be measured using viscosity monitoring.

Viscosity monitoring is useful with a type of measurement to be described below in which there is established a constant flow of liquid into and from the reaction volume 66. An increase in the viscosity of the liquid within the reaction volume 66 results in increased drag and in retardation of motion of the cover.

As an alternative to the use of a strain gage 248 in viscosity measurements, there may be used a piezoelectric element mounted on the cover 10.

Figure 38:
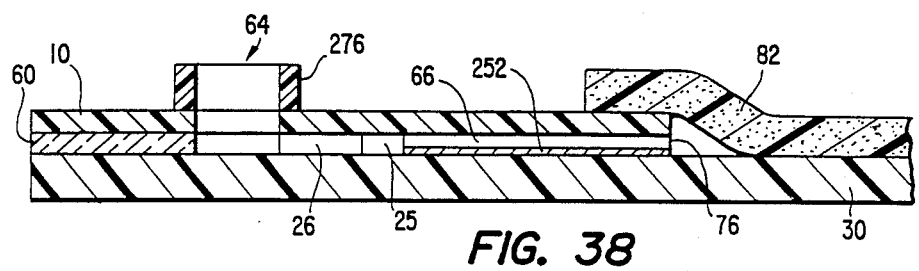
FIG. 38 is a longitudinal cross-sectional elevation of a reaction slide augmented for performing a continuous flow measurement and having a reagent-containing layer disposed on the base.

As has been noted above, a reaction slide according to the current invention provides for the storage of a pre-measured amount of reagent. One manner of providing for the presence of a reagent has already been described in which a liquid reagent is placed in the reaction volume and then dried, such that the dried reagent coats the interior surfaces of the reaction volume. Other methods will now be described with respect to FIGS. 38–41 and 61. Shown in FIG. 38 is a longitudinal cross-section of a portion of a reaction slide 1 according to the current invention. There is shown a reagent-containing layer 252 disposed on the base 30 in the region of the reaction volume 66. If desired, the reagent-containing layer 252 may extend further to the left than shown, occupying the regions of the tapering walls 25, the conduit 26 or even extending into the sample well 64. Although the illustrated reaction slide is of the type that vents laterally (that is, there is no vent opening in the cover 10), a reagent layer 252 may be used with any embodiment.

Figure 39:
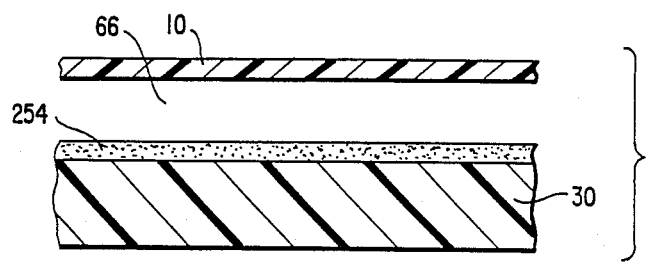
FIG. 39 is a fragment of FIG. 38 in the area of the reaction space, in which the reagent-containing layer is in the form of a reagent-containing gel.

FIG. 39 is a fragmentary vertical cross-section taken in the region of the reaction volume of FIG. 38 and illustrating a first specific embodiment of a reagent-containing layer 252 as shown in FIG. 38. In particular, the reagent containing layer 252 is in the form of a reagent-containing gel 254.

Figure 40:
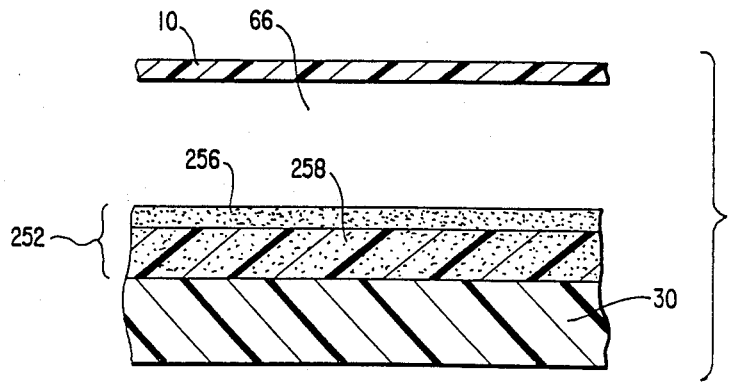
FIG. 40 is a fragment of FIG. 38 in the area of the reaction space in which the reagent-containing layer is in the form of a reagent-containing membrane disposed above a liquid absorbing matrix.

FIG. 40 is a similar view, showing a second embodiment of a reagent-containing layer 252. In particular, the layer 252 comprises an upper layer 256 of a thin porous hydrophilic (semipermeable) membrane. The membrane 256 is attached to the second layer 258, which is in the form of a liquid absorbing matrix (LAM).

The embodiment shown in FIG. 40 is especially useful for plasma separation when whole blood is used as the sample. In particular, plasma is drawn through the membrane 256 and into the LAM 258, where it is stored. Further details of such an assay will be described later. Variations of this embodiment are possible, according to which the layer 252 may comprise the LAM 258 having thereon a thin coating of polymer to provide a finer pore structure at the upper surface of the LAM, such that the upper skin of the LAM performs the same function as performed by the membrane 256. That is, the fine pores of the thin polymer coating exclude cells but admit plasma. Alternatively, the entire layer 252 may consist of a single layer of a fine pore sponge.

Figure 41:
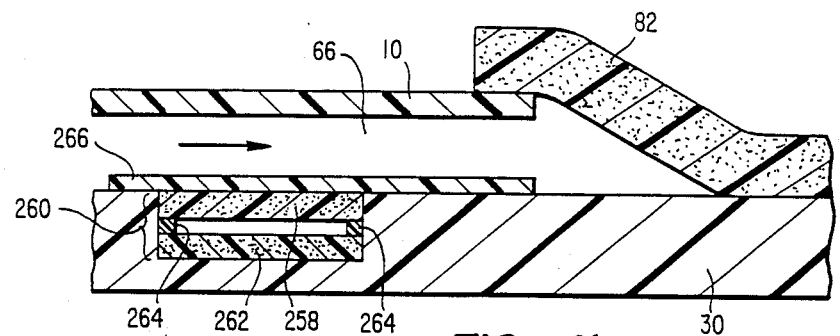
FIG. 41 is a fragment of FIG. 38, modified by the addition of a recess in the base to accomodate a liquid absorbing matrix and a second reagent-containing layer.

FIG. 41 is a fragmentary vertical cross-section of an additional embodiment of a reaction slide according to the current invention, taken in the vicinity of the reaction volume 66. This embodiment also is useful where whole blood is the sample and is used for initiating a reaction at a desired time after plasma separation is achieved. A cavity 260 is formed in the base 30 of the reaction slide. Disposed in the bottom of the cavity 260 is a reagent-containing layer 262, on top of which is an inert annular spacer 264. Disposed above the spacer 264 is a LAM 258, there thus being formed a gap between the LAM 258 and the reagent-containing layer 262. Plasma-separating membrane 266 is disposed in the reaction volume 66 in contact with the LAM 258.

With whole blood in the reaction volume 66, plasma will be drawn through membrane 266 and stored in LAM 258. After such separation is achieved, a reaction may be initiated at any desired time by manually or automatically (for example, as with a solenoid driver) pushing down on cover 10 to cause contact between the LAM 258 and the reagent-containing layer 262. Such contact will initiate a reaction at the desired time.

Figure 61:
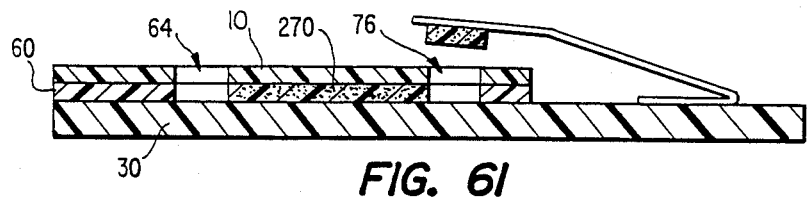
FIG. 61 is a longitudinal cross-sectional elevation of a reaction slide in which a reagent-containing matrix fills a substantial portion of the reaction space.

FIG. 61 is a longitudinal cross-sectional elevation of a reaction slide according to the current invention, showing yet an additional method of incorporating a reagent into a reaction slide. Reaction volume 66 is filled with a permeable polymeric matrix 270 having a reagent distributed throughout the matrix. It is a matter of choice whether or not the matrix 270 extends to the right as shown in the drawing into the region of the vent 76 or all the way to the left in the drawing as far as the sample well 64. The use of such a dry porous space-filling reagent in the reaction volume provides capillary or interstitial fine structure that is capable of controlling the filling beyond the control provided by the capillary flow ordinarily arising from the spacing of the cover 10 and base 30.

Figure 42:
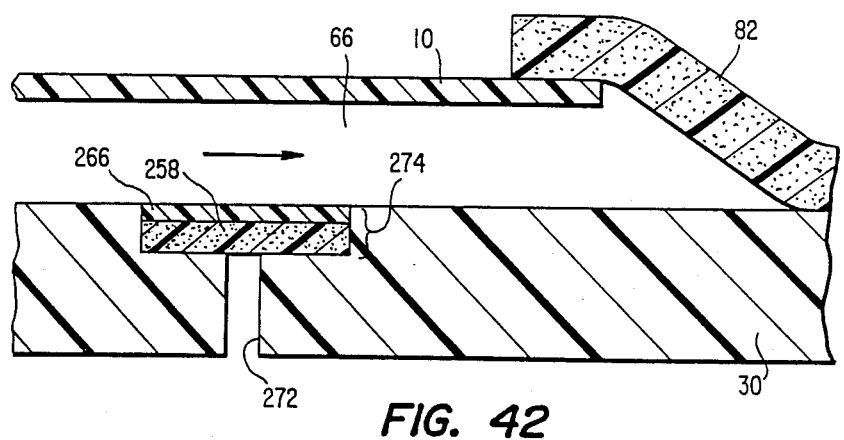
FIG. 42 illustrates a reaction slide modified for use in initiating an assay.

It will be noted that performing an assay typically begins with the introduction of a sample into a sample well 64 of a reaction slide. FIG. 42 illustrates an additional embodiment of a reaction slide according to the current invention, the embodiment being useful as a "processing device" for initiating an assay at any desired time by depositing a sample into a sample well of another reaction slide at the desired time.

A passage 272 extends from the lower surface of base 30 upwardly to a recess 274 of greater lateral dimensions. Disposed in the recess 274 are a plasma separating membrane 266 and a LAM 258. With whole blood filling the reaction volume 66, plasma passes through membrane 266 and is collected in LAM 258. Either before or after such separation, the slide shown in FIG. 42 is positioned above a second reaction slide in which the assay is to be performed. In particular, it is positioned such that the passage 272 lies directly above the sample well 64 of the second reaction slide. At the desired time, the cover 10 of the slide shown in FIG. 42 is depressed, and such depression will result in the expulsion of a drop or droplets of plasma from LAM 258, through passage 272 and into the sample well of the second reaction slide to initiate the assay.

As has been discussed above, the various embodiments of reaction slides according to the current invention are useful in performing a variety of assays. A prothrombin time determination has been described above. More specific examples are given below in Examples 1–7. There will now be described what may be called a continuous flow assay involving the separation of cells in a flowing stream. The embodiments of FIGS. 38–41 are especially useful for such assays. An important conceptual difference between such assays and those in which the sample remains in the reaction volume 66 (such as the prothrombin time determination) is that, in a continuous flow assay, there is a comparatively larger volume of sample available in the sample well 64, and a continuous flow is established from the sample well 64 to the LAM 82. To this end, it may be desirable to enlarge the available volume of the sample well. FIG. 38 shows one way in which the sample well 64 may be enlarged. In particular, annular sample well extender 276 is fixed atop the cover 10 of the reaction slide 1 to increase the volume of the sample well 64. Other means of accomplishing this result may present themself to those of ordinary skill in the art.

A liquid sample is placed in the sample well 64. This sample rapidly flows to the right in FIG. 38, filling the conduit 26 and the reaction volume 66. Upon contact of the liquid with the LAM 82, a flow condition is set up whereby the liquid is pulled in and flows continuously into the LAM 82 until the sample well 64 is exhausted.

The established laminer flow condition is advantageous for analysis or processing of certain types of samples, such as samples with suspended particles (including but not limited to whole blood). A characteristic of the continuous flow is that suspended matter moves away from the top, bottom and side walls of the passage in which it flows and toward the center of the stream. Such material accordingly does not participate to a substantial degree in chemical, enzymatic or immunological reactions caused by reagent-containing layers 252. Thus, the laminar flow condition driven by the LAM 82 provides a separation step. Color development may be read in the reagent layer 252 in a variety of ways, such as the use of reflectance measurement technology illustrated in FIG. 28.

In a continuous flow measurement, when the sample is blood, an embodiment similar to those described above in regard to FIGS. 40 and 41 is desirable. The pore structure used for passing plasma and excluding blood cells should be such that the pores have a size of approximately 1.2 microns or less. For the use of whole, non-anticoagulated blood, anticoagulant may be present, if required, in LAM 82 and possibly in the vicinity of or contained within the reagent-containing layer 252.

Separation of cells (or particulates) in a flowing stream from the medium in which the cells are suspended may be achieved under the appropriate flow conditions, since the cells migrate away from the walls of the conduit and toward the center of the stream. As disclosed by B. A. Solomon (Membrane Separations: Technological Principles and Issues, Vol. XXVII, Trans. Am. Soc. Artif. Organs 1981 pp. 345–350), blood flow sustained parallel to the plane of a suitable membrane allows plasma to be drawn through the pores of the membrane without damaging the cells, due to the tendency of cells to migrate away from the membrane surface. In the present invention, the sustained transverse flow is achieved not by pumping or vacuum (pressure differentiation) induced by mechanical means but through the use of a fine capillary or absorbent structure (LAM) to remove liquid (e.g., blood) and thereby to cause movement or flow in a direction parallel to the plane of the membrane. At the same time, a capillary action through the membrane and into a second liquid absorbing matrix (LAM) is achieved to collect the separated blood plasma on the opposite side of the membrane. The reaction volume dimensions provide a conduit or chamber such that the flowing liquid develops shear forces sufficient to minimize passage of cells through the membrane and hence to minimize cell destruction. The second LAM may contain reagents for performing an assay. The second LAM may be utilized only for collection (and could contain anticoagulants, preservatives, etc.). Diagnostic reagents could be bound to the membrane or contained in another layer adjacent to the membrane or LAM.

The art of removing a plasma sample from whole blood using a separating matrix and later contacting it at a precise time with a reagent layer has been described for use with a gel or porous medium (Oberhardt, B. J., U.S. Pat. No. 4,288,228, Sept. 8, 1981) and later (by Vogel, P., et al., U.S. Pat. No. 4,477,575, Oct. 16, 1984) for use with a glass fiber layer. The present invention shows yet another way to achieve the objective of plasma separation and reaction initiation at a precise time.

Figure 43:
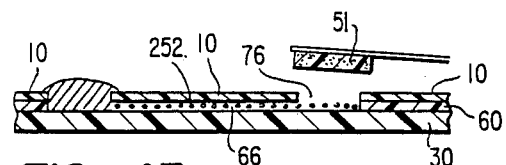
FIGS. 43-51 are longitudinal cross-sectional elevations of a reaction slide during various stages of an ELISA type immunoassay.
Figure 52:
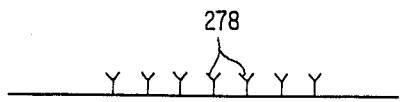
FIGS. 52–60 schematically illustrate the physiochemical conditions within the reaction space during each of the stages illustrated in FIGS. 43–51.

FIGS. 43–60 show how a reaction slide may be utilized to perform an assay involving a bound reagent, several added reagents, and washing steps. An ELISA type immunoassay and the embodiment of FIG. 6 are used as an example. In FIG. 43, a sample to be analyzed is placed in the sample well. At the bottom of the reaction space is a layer 252 of covalently attached antibody molecules 278. This layer is better visualized in FIG. 52, to the right of FIG. 43. A moveable sponge or LAM 51 which forms part of the disposable reaction slide is situated on the base and fastened by any of a variety of mechanisms to allow it to be moved by an external mechanical driver to alternately engage and disengage the LAM from the vent 76 of the reaction volume 66.

Figure 44:
Figure 45:
Figure 53:
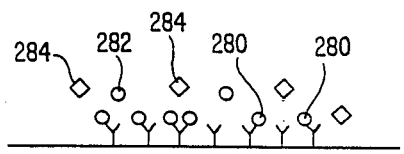
Figure 54:
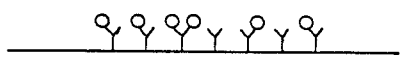
Figure 55:
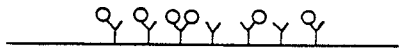
Figure 56:
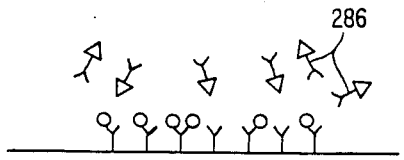
Figure 57:
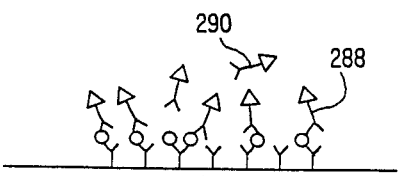
Figure 49:

FIG. 44 shows the sample filling the reaction volume. FIG. 53 shows greater detail indicating the capture of antigen molecules 280 by the bound antibody 278. Some unbound antigen 282 and other molecular species 284 are shown, as well. In FIG. 45, the LAM is depressed to remove all liquid from the system and is subsequently returned to its original position. Emptying the reaction volume of liquid can be monitored electro-optically, as previously described. In FIG. 54, the antibody molecules with captured antigen are shown. Although not indicated, it is also possible to introduce into the sample well a buffer liquid and then repeat the step shown in FIG. 45 to achieve a better washing. This washing step with buffer, which is well known in the art, could be repeated, if necessary.

Figure 46:
Figure 47:
Figure 48:
Figure 50:
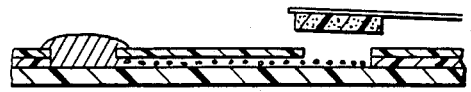
Figure 51:
Figure 58:
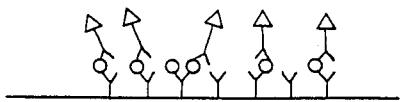
Figure 59:
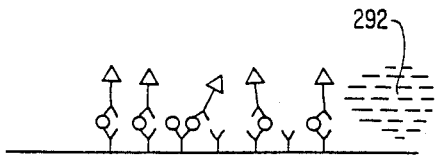
Figure 60:
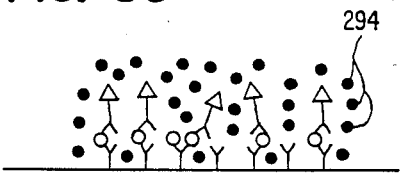

In FIG. 46, reagent is introduced. This second reagent (the first being the bound antibody) is rapidly drawn in (FIG. 47) and consists of an antibody-enzyme conjugate 286. After a short incubation (FIGS. 48 and 57), some of the antibody enzyme conjugate molecules become bound 288 to a second site on the antigen molecule (with different specificity than the first site) and some conjugate molecules remain free 290. The liquid is then removed in FIG. 49 (as in FIG. 45) with the possible incorporation of additional washing steps with a buffer. In FIGS. 50 and 59, a developer reagent consisting of a fluorogenic or chromogenic substrate 292 or combination of substrate and developer dye is added. FIG. 51 shows the filling of the reaction volume, and FIG. 60 shows the development of chromophores 294 or other optically detectable species.

Thus, it is shown that the LAM-reaction slide can allow a precise multistep immunoassay to be conducted with imprecise pipetting steps and simplified wash steps. This could be combined with forced convection to facilitate reactions in FIGS. 53, 56 and 59 (as shown in previous embodiments utilizing internal mixing). Of major significance is that labor can be significantly reduced with the use of simple and inexpensive instrumentation performing operations on and interacting with the reaction slide.

As was the case with the embodiment illustrated in FIG. 13, the configuration of the LAM as illustrated in FIGS. 43–51 may, if desired, be modified by having the LAM overlap over part of cover 10. In this other embodiment, the LAM is situated above the base and is in contact with the cover. Removal of fluid from the reaction chamber is achieved by compressing the LAM down toward base 30 so that contact is established between the LAM and the fluid in the reaction volume.

Figure 62:
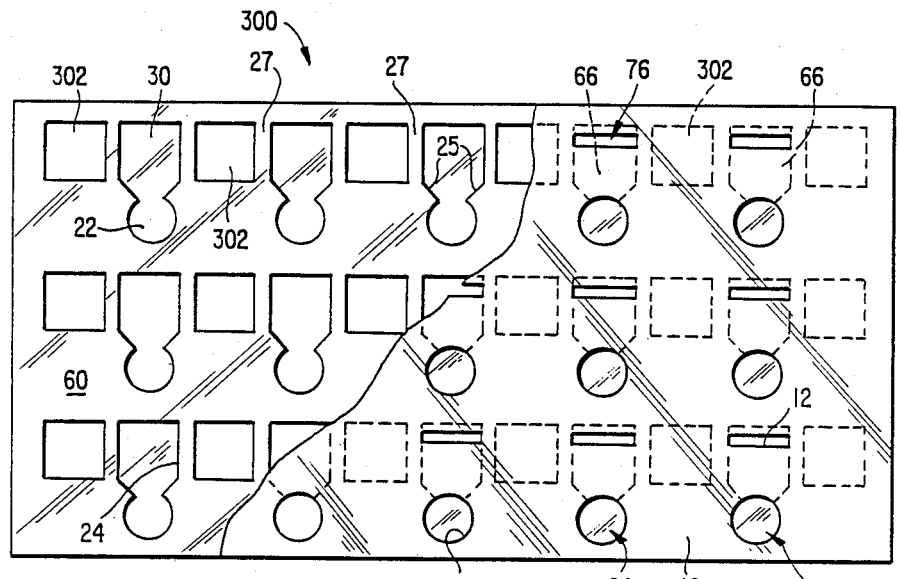
FIG. 62 is a top view, with the cover partially removed, of independent reaction spaces disposed on a common base.

Shown in FIG. 62 is a top view of a first embodiment of a reaction slide of a type having plural reaction volumes. Cover 10, shown partially cut-away in the figure, is provided with openings 14, used in forming a plurality of sample wells 64, and rectangular openings 12 forming vents 76 leading to the reaction volumes 66. The spacer 60 may be any of the types previously described. In the illustrated embodiment, there are provided in the spacer 60 a plurality of sample receiving openings 22, which also form part of the sample wells 64. Each sample receiving opening 22 communicates with a reaction space 24, also cut from the spacer 60. As in the preceeding embodiments, the reaction space 24 is used in conjunction with cover 10 and base 30 to form a plurality of reaction volumes 66. Tapered walls 25 are provided communicating the sample receiving opening 22 and reaction space 24.

Disposed beneath the spacer 60 is a base 30, which is visible through the sample receiving openings 22 and reaction spaces 24.

A plurality of slots 302 are cut through both the spacer 60 and base 30 and disposed adjacent each reaction volume 66. The slots 302 are configured to receive external optical waveguides that extend upwardly through the base 30 and spacer 60 for carrying light to and from the internal waveguides 27 formed between the slots 302 and the reaction volumes 66. As above, such light may be used for measurements using colorimetry, light scatter, and similar measurements.

It may be seen that the embodiment 300 provides dense packing to achieve more reaction spaces per unit area of common base 30.

The embodiment 300 may be used with a single set of external waveguides, one mixing station and one LAM actuating mechanism (not shown), each of which may be indexed from space to space, as required, to service designated reaction volumes 66. In the alternative, there may be used a plurality of fixed external waveguides, mixing stations and LAM actuators, and these may be used independently or simultaneously.

As a variation, individual LAM's may be provided on a strip extending from left to right in the drawing, such that depressing the strip causes the LAM's to withdraw liquid from the vents 12 of each reaction volume 66 in a single row. In FIG. 62, three such LAM strips would be used, as there are three rows of reaction volumes.

Samples may be added to the sample wells 64 independently or simultaneously.

Figure 63:
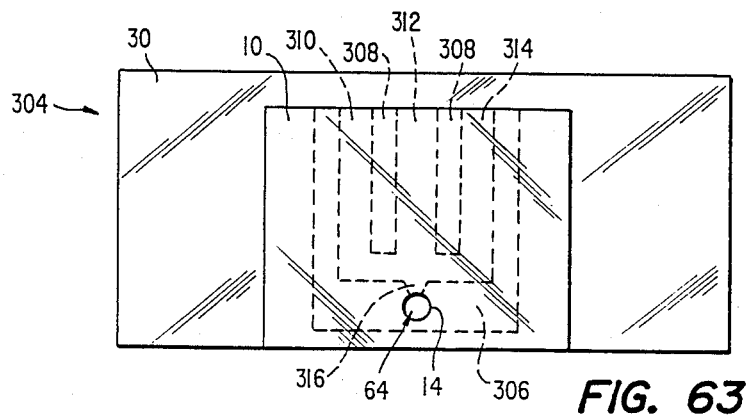
FIG. 63 is a top view of a reaction slide of the parallel flow type having three reaction spaces.

Shown in FIG. 63 is a top view of a second embodiment 304 of a reaction slide having plural reaction spaces. There is provided a solid base 30, a cover 10 having a sample receiving opening 14 formed therein, and a spacer disposed between cover 10 and base 30, the spacer being formed of a U-shaped member 306 and two dividers 308. The elements 306 and 308 are of uniform height such that cover 10 is uniformly spaced from base 30.

The sample well 64 extends downwardly into the U-shaped member 306 and communicates through passage 316 with each of three reaction volumes 310, 312 and 314. Each of the three reaction volumes vent laterally, which is toward the top of the drawing. If desired, an external LAM 82 may be provided as shown in FIG. 13. A separate LAM may be provided for each reaction volume, or a single LAM may serve all three reaction volumes.

Addition of liquid sample to sample well 64 causes rapid filling of all three reaction volumes. The center volume 312 fills slightly faster due to its location adjacent passage 316. If desired, the sample well 64 may be relocated, or other geometric changes may be made to cause each of the reaction volumes 310, 312 and 314 to fill at the same rate.

Figure 64:
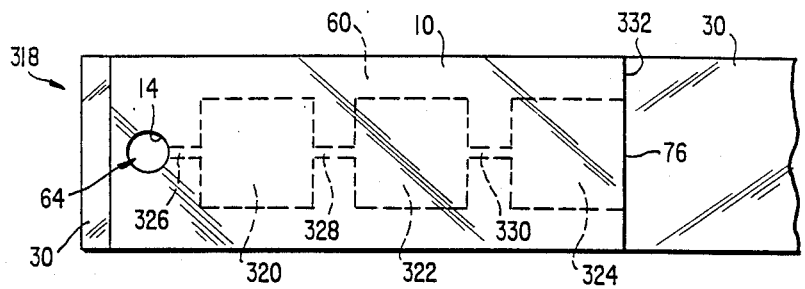
FIG. 64 is a top view of a reaction slide of the serial flow type having three reaction spaces.

Shown in FIG. 64 is a top view of a third embodiment 318 of a reaction slide having plural reaction volumes. Cover 10 is provided with a sample receiving opening 14, which forms part of the sample well 64. The spacer 60, of uniform height and disposed between cover 10 and base 30, is provided with a cut-out forming three reaction volumes 320, 322 and 324. Reaction volume 320 communicates with sample well 64 through passage 326, also cut into the spacer 60. Passage 328, cut into the spacer 60, communicates reaction volume 322 and reaction volume 320. Passage 330 communicates reaction volume 324 and reaction volume 322. The distal end 332 of the spacer 60 is open, such that reaction volume 324 vents laterally, to the right in the drawing. A LAM may be provided as shown in FIG. 13.

It may be seen that the reaction volumes fill sequentially from sample well 64. When it is desired to remove sample from the reaction volumes, a LAM applied to the distal end 332 of the spacer 60 will first empty reaction volume 324. It has been found that, if the LAM is suddenly removed, it is possible to bring about the step-wise transfer of sample from reaction volume 320 into reaction volume 322 and the simultaneous movement of sample from reaction volume 322 into reaction volume 324. Such action may be used to facilitate sequential rections through the translation of contents of reaction volumes laterally through any desired number of sequential reaction volumes.

Figure 65:
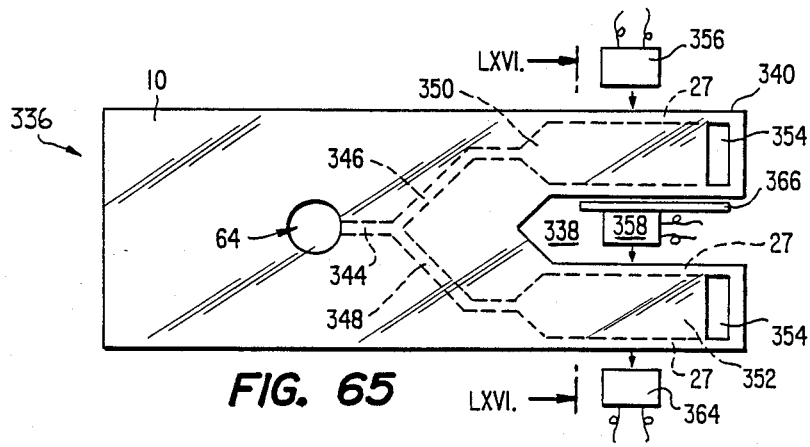
FIG. 65 is a top view of a reaction slide of the parallel flow type having two reaction spaces, also showing light sources and detectors.
Figure 66:
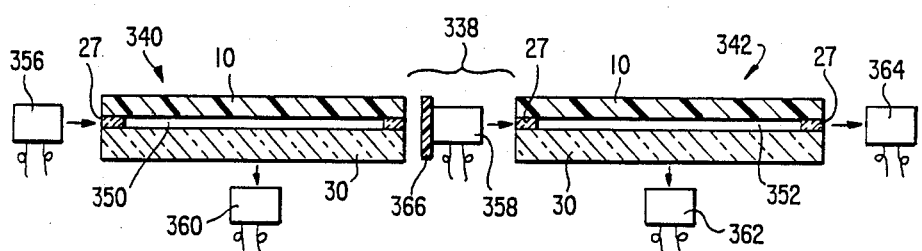
FIG. 66 is a transverse elevational cross-section taken on line LXVI—LXVI of FIG. 65. Together.

FIGS. 65 and 66 show a fourth embodiment 336 of a reaction slide according to the current invention, the reaction slide 336 having plural reaction volumes filled by parallel filling. Among the uses of reaction slide 336 is that it is useful in conducting a Plasminogen Activator assay. Also shown in FIGS. 65 and 66 is instrumentation useful in conducting the tissue plasminogen activator (TPA) assay.

In reaction slide 336, the base 30, the spacer and the cover 10 have been cut out as shown at 338 to form first and second legs 340, 342. The cover 10 is provided with an opening for the sample well 64 and openings for each of the vents 354 that communicate respectively with first reaction volume 350 and second reaction volume 352. The spacer is cut out to form the sample well 64 and to form common conduit 344 which branches to form first and second branched conduits 346, 348, the branched conduits respectively leading to the reaction volumes 350 and 352. As in certain of the previous embodiments, the spacer is transparent to provide internal waveguides 27 adjacent the reaction volumes. It will be seen that a sample placed in sample well 64 will be drawn by capillary action through common conduit 344 and will then divide, proceeding through branched conduits 346, 348 and into the reaction volumes 350, 352.

Also shown in FIGS. 65 and 66 are first light source 356, second light source 358, first scatter detector 360, second scatter detector 362 and transmission detector 364. Light shield 366 protects the second reaction volume 352 from receiving radiation from first light source 356. It may be seen that light from first and second sources 356, 358 respectively enters first and second reaction volumes 350, 352, where some of it is scattered at 90° and passes through base 30, whereafter the scattered light is detected at 360 and 362. Transmission detector 364 detects that portion of the light from source 358 which has been neither scattered nor absorbed in reaction volume 352.

The various embodiments of reaction slides according to the current invention may be provided with apparatus for accomplishing "selective flow", according to which the filling of a reaction volume from a sample well may be delayed for any desired length of time after a sample has been placed in the sample well. Such selective flow may be accomplished by selective venting, as will be described with reference to FIG. 67, or by use of a pinch valve, as will be described with reference to FIGS. 68 and 69.

Figure 67:
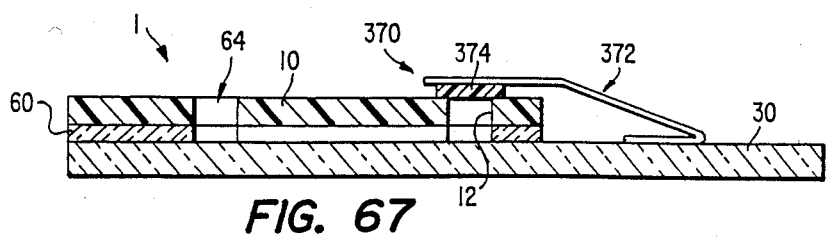
FIG. 67 is a longitudinal cross-sectional elevation of a reaction slide having a vent cover useful in selective venting.

In selective venting, capillary action is initially prevented by blocking the downstream egress of air. This is most easily accomplished in those embodiments of a reaction slide in which the venting is accomplished vertically, through an opening through the cover. FIG. 67 is a vertical longitudinal cross-section of a representative reaction slide 1. The reaction slide 1 includes a vent cover assembly 370, the vent cover 370 including a cover support 372 and an elastomeric pad 374 attached to the pad 374 is not a LAM and the cover support 372. Elastomeric pad 374 may be made, for example, of silicone or latex. Structurally, the cover support 372 is similar to the LAM support 52 described above in relation to FIG. 6, except that the pad 374 is not a LAM and the cover support 372 continually biases the pad 374 against the vent opening 12, blocking it.

A sample placed in sample well 64 will remain in the sample well until such time as the pad 374 no longer blocks the vent. Such unblocking of the vent may be brought about by lifting cover support 372. Such lifting may be accomplished manually, mechanically or electromechanically.

Modifications are possible. For example, the cover support 372 need not be attached to base 30 but may, instead, take the form of a straight element extending to the right in the figure. Any appropriate means may be used to grasp the support 372 and lift it. In such a case, it may be desirable to provide a slight adhesive bond between the pad 374 and cover 10 to prevent premature displacement. In the alternative, a vent cover assembly may be contained in an instrumentation housing, completely separate from the reaction slide 1. When the reaction slide is inserted into the housing, the vent cover assembly may be brought downwardly to cover the vent.

Figure 68:
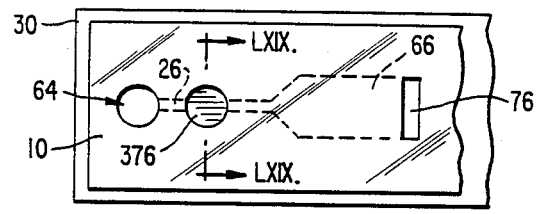
FIG. 68 is a top view of a reaction slide provided with a pinch valve.
Figure 69:
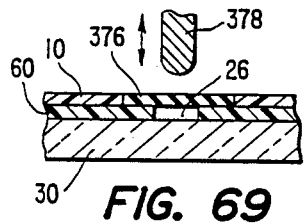
FIG. 69 is a section taken on line LXIX—LXIX of FIG. 68, also showing a push rod for actuating the pinch valve.

FIGS. 68 and 69 illustrate a pinch valve mechanism. Elastomeric disk 376 is fixed in an opening in cover 10, the disk 376 being disposed directly above conduit 26 which connects the sample well 64 and the reaction volume 66. Pinch rod 378, which may be attached to a control mechanism in an instrumentation housing, is vertically movable so as to descend and press the elastomeric disk into the channel 26, thereby blocking flow from the sample well 64. At any desired time, the pinch rod 378 may be raised to allow the sample to reach the reaction volume 66.

With the incorporation of selective flow by selective venting or a pinch valve mechanism, or both, it is possible to send a liquid or liquids to a reaction volume at a predesignated time or to move liquid streams out of one reaction volume and into another at a predesignated time, as described below. It also is possible to stop the flow of liquid into a reaction volume, for example, when it is partially filled. Among the possible applications are as follows:

A. A chemical reaction may be initiated at a specific time, such as after a prior reaction has taken place (e.g., for diagnostic assays).

B. Mixing of two liquids is possible and easy to control, as also described below.

C. As described below, cascading of reaction spaces may be controlled.

D. By mixing two liquids, it is possible to perform dilutions (sequential dilutions).

Figure 70:
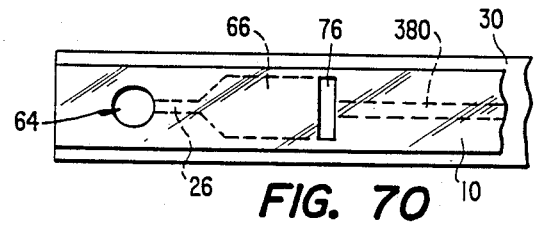
FIG. 70 is a top view of a reaction slide having an auxiliary conduit.
Figure 71:
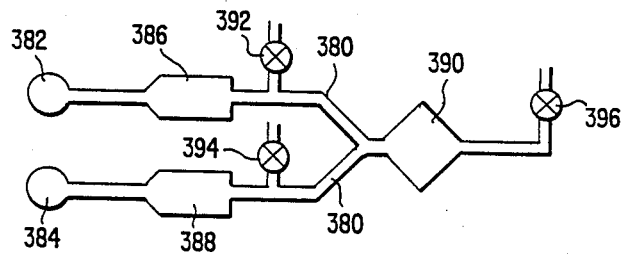
FIG. 71 is a schematic representation illustrating how two liquids may be selectively introduced into a common chamber.

FIG. 70 is a fragmentary top view of a reaction side in which an interconnecting conduit 380 is formed in the spacer. In the drawing, the left end of conduit 380 communicates with reaction volume 66. The conduit extends to the right for transferring liquid from reaction volume 66 to one or more additional reaction volumes disposed on the same base 30. FIG. 71 schematically illustrates one use for such an interconnecting conduit 380.

As schematically represented in FIG. 71, a reaction slide may comprise first and second sample wells 382, 384, first and second reaction volumes 386, 388 respectively fed from the sample wells 382, 384, and third reaction volume 390 fed by two interconnecting conduits 380 which respectively communicate with the reaction volumes 386, 388. All of these elements may be a part of the same reaction slide. That is, all of them may be disposed on a common base 30 and formed by a single appropriately-cut spacer. Elements 392, 394 and 396, functionally and schematically represented as valves, may physically take the form of three separate vent cover assemblies for selective venting as shown in FIG. 67.

According to FIG. 71, two separate liquids may first be introduced into reaction volumes 386 and 388 from their respective sample wells 382, 384, at any desired time. Thereafter, the two liquids are mixed in volume 390 for further reaction or measurement or both.

For example, with vents 392, 394 and 396 closed, sample well 384 may be filled with a sample and sample well 382 may be filled with a reagent. Dry reagents are disposed in the reaction volumes 386, 388 and 390, having been put there previously. At a desired time, vents 392 and 394 are opened to allow the reaction volume 386 to fill with reagent from sample well 382 and to allow the reaction volume 388 to fill with reagent from 384. Thereafter, incubation or mixing or both occurs in reaction volumes 386 and 388, for a preselected time through the use of previously-described means. Then, with vents 392 and 394 closed, vent 396 is opened to draw fluid through the two interconnecting channels 380 into reaction volume 390. The reaction volume 390 may have a volume equal to or less than the combined volumes of 386 and 388. Mixing may be carried out in 390, and a reaction therein may be monitored by any of the previously-described means for monitoring a reaction. If desired, reaction volumes 386 and 388 may similarly be monitored.

If desired, the two interconnecting conduits 380 may be dimensioned such that they compensate for differences in viscosity between the liquids and the two reaction volumes. For example, if the liquid in volume 386 is more viscous than that in volume 388, and if it is desired to mix both liquids in equal proportions in 390, then the upper interconnecting conduit 380 in the drawing may be made wider than the lower interconnecting conduit 380 to produce substantially equivalent flow under capillary flow driving forces in the system. Light scatter sensors may be used to monitor the three reaction volumes to determine when the volumes are filled or empty, to determine how fast a volume is filling, and to operate controls to open and close the vents to start and stop the flow.

It will be understood that the same results may be accomplished using another means for achieving selective flow. For example, pinch valves may be incorporated both upstream and downstream of each of the reaction volumes 386, 388.

FIG. 71 is a simple example of cascading, more complex examples of which will now be described.

Figure 72:
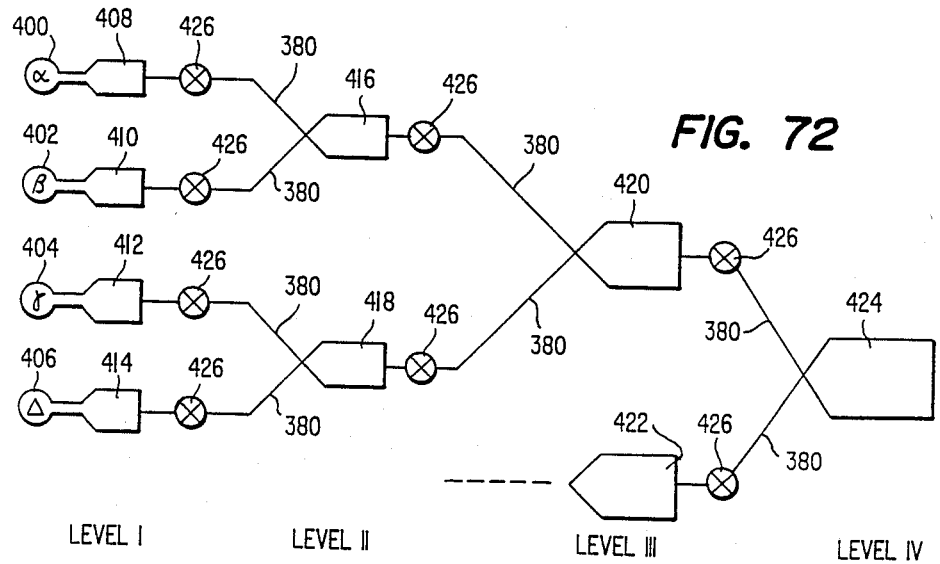
FIGS. 72–74 schematically illustrate various forms of cascading.

FIG. 72 shows four levels of cascading, which will be referred to as level I, level II, level III and level IV. Level I is represented by reaction volumes 408, 410, 412 and 414. Each of these reaction volumes is respectively supplied from an associated sample well 400, 402, 404 and 406. Reaction volumes 408 and 410 feed reaction volume 416 through interconnecting conduits 380. Similarly, reaction volumes 412 and 414 feed reaction volume 418 through an additional set of interconnecting conduits 380. Selective flow is provided by pinch valve mechanisms 426. Reaction volumes 416 and 418 represent level II. By similar structure, reaction volumes 420 and 422 represent level III, and reaction volume 424 represents level IV. If desired, additonal reaction volumes may be provided as indicated by the dashed line extending to the left of reaction volume 422 in the drawing. The size of the reaction volume at level IV is typically, but not necessarily, twice as great as the combined volumes of the reaction volumes at level III. Similarly, the combined volumes of the reaction volumes at level III are typically two times as great as those at level II. Each reaction volume may be empty or may contain a dry reagent. Any or all reaction volumes may be subjected to mixing by previously-described means and may be configured for liquid removal by a LAM. Any or all reaction volumes may be monitored by previously-described methods and also inspected by automated light microscope or by eye.

At level I, each of the liquids may be reacted and studied or monitored. A decision may be made thereafter to move any or all of the liquids to level II. Depending upon the nature of the decision made, further measurement may be made in reaction volume 416, 418, or both, where a further reaction may be monitored.

More specifically, if the contents of the sample wells 400, 402. 404 and 406 are respectively represented as $\alpha$, $\beta$, $\gamma$, and $\Delta$ any or all of these liquids may be reacted at level I. Thereafter, at level II, $\alpha$ and $\beta$ may be reacted together in reaction volume 416. In the alternative, $\alpha$ may be sent alone to level II and reacted with dry bound reagent in reaction volume 416. The liquid may then be absorbed by a LAM to empty the reaction volume 416, after which time may be admitted to reaction volume 416 to further react with products captured by the bound reagent in reaction volume 416. Similar procedures and decisions may be made with regard to samples $\gamma$ and $\Delta$.

The resultant product in reaction volume 416 may be sent to reaction volume 420, either alone or in admixture with a liquid from reaction volume 418. The process then continues analogously until reaction volume 424 is filled with liquid from reaction volume 420 or from 422 or from both.

Figure 73:
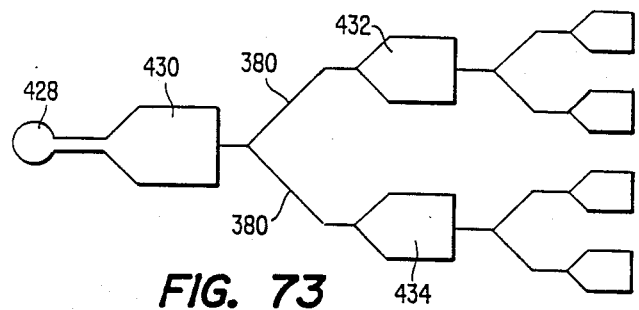

FIG. 73 schematically illustrates cascading in an order that is inverse from that shown in FIG. 72. In particular, a single initial sample placed in sample well 428 and initially reacted in reaction volume 430 may later be channeled to either or both of downstream reaction volumes 432, 434, and so forth. Selective flow in FIG. 73 may be accomplished by pinch valve mechanisms or by selective venting, as described above.

Figure 74:
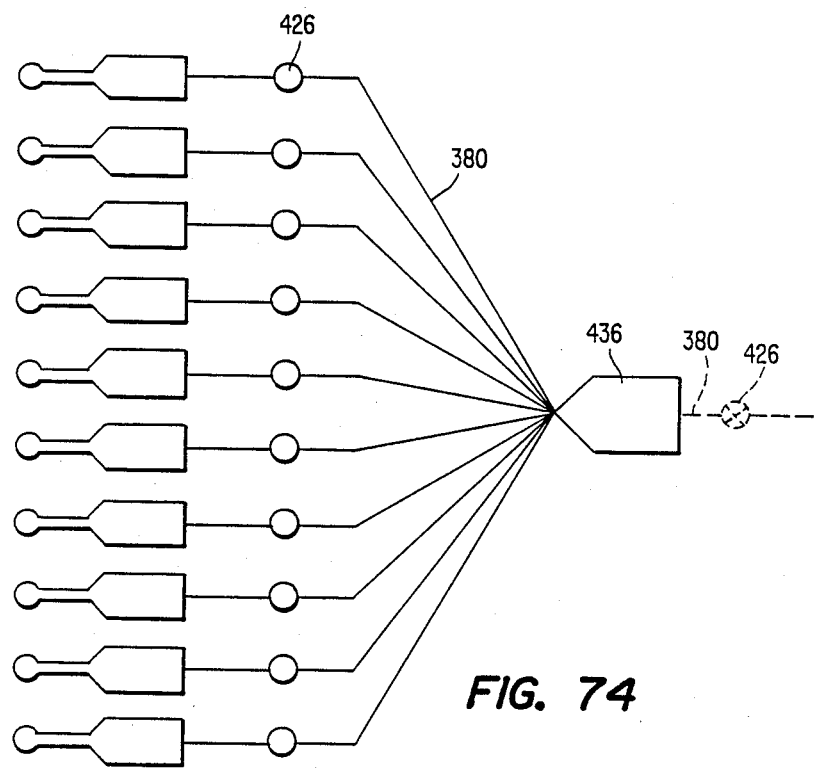

Yet a further example of cascading is shown schematically in FIG. 74, in which a plurality of sample wells and associated reaction volumes selectively feed a single reaction volume 436, and the product of a reaction in the volume 436 may, if desired, be further sent to yet additional reaction volumes, is illustrated by the interconnecting channel 380 shown in phantom. Such additional reaction volumes may be disposed in serial, in parallel or cascaded.

In general, in regard to FIGS. 70-73, it should be noted that the sizes of the sample wells and reaction volumes should be such as to provide a sufficient volume of liquid to fill whatever volumes are anticipated will be needed. For example, in FIG. 73, it may be necessary for the volume of sample well 428 to be sufficient to fill each of the illustrated reaction volumes. One means of providing such a sufficient volume of sample has been described above in the form of the enlarged sample well of FIG. 38.

Thus, it may be seen that cascading of reaction volumes allows reactions to be initiated and monitored and, based upon the results obtained and decisions made (e.g., made by computer), cascading further allows for additional or subsequent reactions to be initiated, controlled and monitored using reaction products from the first reactions or samples from the first reactions. This provides the capability of performing complex assays with simple apparatus. It also allows a "tree assay" to be performed. That is, it allows for a series of branched assays to be performed in parallel fashion but connected via branch structure to a "tree" to answer a specific question. For example, the first reaction volume could answer the question: "acid or base?" The sample or reaction products could then be sent to one of two reaction volumes, one to perform further tests on "acids" and one to perform further tests on "bases", and so forth. Ultimately, highly specific information may be known about the analyte.

Another application might be in finding an antibody or antigen molecule which is specific for a given antigen or antibody. In this case, antibodies or antigens may be placed (or bound) in the reaction volumes, and the appearance of reactivity may be monitored and used as a basis for selecting other reactions. Similar applications could apply to DNA, DNA-probe reactions, enzyme-substrate reactions and so forth.

Specific examples will now be given disclosing the use of various embodiments of a reaction slide according to the current invention. Other features of this invention will become apparent in the course of these exemplary embodiments which are given for illustration of the invention and are not intended to be limiting thereof.

EXAMPLE 1

A 0.020 inch thick (3.0×0.75 inch) strip of polycarbonate was prewashed with distilled water and dried. Upon this strip or base was placed a two-layer spacer consisting of two pieces of a double-sided tape made from two thin sheets of unplasticized polyvinyl chloride, each sheet previously having been coated on both sides with medium-firm pressure sensitive acrylic adhesive. The two-layer overlay had previously been cut out in the center to create a sample well, conduit, reaction space, and vented area, as may be seen in FIG. 5. The double overlay composite plus adhesive coatings was of sufficient thickness to provide a final spacing between the base and cover of 0.007 inches. The cover was cut from 0.010 inch precleaned polycarbonate sheet and included a rectangular vent hole and a circular sample well hole. The cover was placed on top of the overlay and pressure applied by means of a small roller to join the overlay to the cover and base.

The reaction volume was filled by means of a small syringe fitted with a 25 gauge needle and positioned so that the solution could flow from the edge of the sample well into the reaction volume. The solution in the syringe was a conventional rabbit brain thromboplastin empirically diluted to an appropriate concentration for use in manual or automated prothrombin time determinations. (Reagent calibration was previously checked by means of a standard manual prothrombin time test using control plasma.) The reaction slide was then frozen at $-70°$ C. and freeze dried.

A blood sample was collected by venipuncture using a 21 gauge needle. An evacuated tube containing sodium citrate, final concentration 3.8 mg/ml was used for collection. The first of two tubes was discarded, in accordance with NCCLS (National Committee for Clinical Laboratory Standards) guidelines. The second tube was centrifuged in a conventional blood bank centrifuge (Clay Adams SEROF UGE) and the plasma decanted. One drop of the plasma sample was placed in the sample well of the reaction slide (after the reaction slide was placed in light scattering measurement apparatus as shown in FIGS. 20 and 21 and prewarmed to 37° C. by means of a feedback controlled surface heater). The plasma sample immediately flowed into the reaction volume. The starting point, as monitored by the scatter detector, was clearly defined, and the endpoint was clearly discernable. This allowed the elapsed time to be readily measured and used to determine prothrombin time (as a percent of control plasma value).

In this case, the light source was a high power light emitting diode (635 nm gallium arsenide/gallium phosphide) and the detector was a cadmium sulfide photoconductive cell. The photocell output was connected to a resistive bridge circuit and a chart recorder. Chart speed was 1 mm/sec, and gain was set at 1 volt full scale. Bridge voltage was 18 volts.

EXAMPLE 2

A reaction slide was prepared as indicated in Example 1 except that it was fabricated using a single sheet of double sided tape as an overlay material (total thickness 0.0035 inches). The reaction slide was tested identically in the same instrument and provided a similar endpoint but with reduced signal intensity and longer lag phase (descending portion of the curve).

EXAMPLE 3

A reaction slide prepared as indicated in Example 1 was placed in the monitoring instrument described in the previous example. A sample of citrated whole blood was added to the sample well. The resulting light scatter curve was observed to show an initial transient increase in scatter intensity, establishment of a new steady state level, and an eventual gradual rise from that level at the onset of a clot. Although the curve was different, the endpoint was similar but with reduced signal intensity. Elapsed time was equivalent to that observed for the plasma curve.

EXAMPLE 4

A reaction slide prepared as indicated in Example 1 was placed in the monitoring instrument described in that example. Samples of citrated whole blood obtained from nine patients undergoing anticoagulant therapy (from a collaborataive study with Memorial Hospital, University of North Carolina, Chapel Hill) were centrifuged, and the plasma samples decanted and tested. A comparison was made of the values obtained with the light scatter instrument and reaction slide versus the clinical laboratory values obtained with a General Diagnostics COAG-A-MATE X-2 Automated Coagulation Analyzer. Although the actual elapsed time values are different for both instruments, an excellent correlation (correlation coefficient=0.95) was obtained. The endpoints were extremely sharp for the reaction slide values, and the clinical laboratory values could be calculated easily from the reaction slide values by using a conversion factor.

EXAMPLE 5

A reaction slide prepared as indicated in Example 1 was placed in the monitoring instrument also described in Example 1. A finger stick was performed using an AUTOLET® Automatic Lancet (Ulster Scientific, Inc., Highland, NY). One drop of blood was placed on the slide sample well. The blood was drawn immediately into the reaction space, initiating the reaction. The prothrombin time endpoint was discernable from the scatter curve in the form of a slope change. As in the case of the previous whole blood example (Example 3), the absolute magnitude of scatter was different (greater) for whole blood than for plasma. However, the elapsed time, and consequently the test result, was essentially the same.

EXAMPLE 6

(a) Reaction slides were fabricated employing spacers as described in Example 1, but with 3, 4, and 5 overlay layers to increase spacer thickness and conseqeuently chamber height of the reaction volume to 0.0105, 0.0140, and 0.0175 inches, respectively. It was observed that reaction slides with reaction volume heights of greater than 0.015 inches were not as reliable for retaining samples and aqueous reagents via capillary forces without leakage.

(b) It was similarly observed that reaction slides prepared as in Example 1 with spacers less than 0.0015 inches thick tended to be difficult to fill and empty of liquid.

(c) A reaction slide prepared as in Example 1 but with cyanoacrylate adhesive and a 0.002 inch thick polyethylene terephthalate sheet did not work well. (Two cyanoacrylate preparations were tried: WONDER BOND Plus, Borden, Inc., Columbus Ohio and Pacer Tech Advanced Technology Series ATS-HC5, Pacer Technology & Resources, Campbell, CA). Waveguide properties were hampered by inhomogeneities in the adhesive, and stiffness led to cracking and leakage during repeated mechanically-induced mixing.

(d) A polyethylene terephthalate sheet coated on both sides with acrylic adhesive (total thickness of 0.004 inches) worked well as a spacer and waveguides and provided the necessary flexibility and leak resistance during filling and during mechanical mixing operations.

(e) A spacer made from acrylic adhesive only (approximate thickness 0.002 inches) provided flexibility, but contained many inhomogeneities, scattering a considerable amount of light and providing a marginally acceptable waveguide.

(f) A reaction slide was fabricated as in Example 1 but employed a 0.050 inch thick, 25×75 mm precleaned glass microscope slide as a base material. In assay performance this material worked extremely well and was comparable to the polycarbonate base.

(g) A reaction slide prepared as in Example 1 but with a 0.007 inch glass cover, carefully cut to shape, worked well in short term studies for light scatter measurement but was prone to cracking during long term mixing studies.

(h) Reaction slides prepared as in Example 1 with reaction volumes of the same dimensions, but with extended cover, spacer, and base (to 2 inches in width) provided attenuated transmitted light from the source into the reaction volume. A low density polyethylene (LDPE) overlay 0.007 inches thick when secured with acrylic adhesive to the cover and base provided a signal which was too weak to be easily distinguished from noise, and therefore this slide was not usable at this distance. The same film was, however, acceptable as a waveguide over a smaller distance (0.125 inches). A polyvinyl chloride overlay (which scattered light less and provided a better waveguide material) was successfully employed in this experiment in place of the LDPE in both instances (at 0.125 and at 2 inches).

(i) A reaction slide was prepared as in Example 1 with 0.1% TRITON X-100 surfactant added to the reagent. Results comparable to Example 1 were obtained, and the reaction slide reaction volume was easier to fill. Prewashing cover and base with the same concentration of surfactant produced similar results.

EXAMPLE 7

A reaction slide prepared as in Example 1 was utilized in a similar experiment with the same plasma sample. In this case, sustained mixing was achieved by means of a 3-inch long push rod glued to and driven by a 3-inch diameter 8-ohm electromagnetic speaker coil. The cylindrical push rod tip diameter was 0.1 inch and pushed against the cover producing oscillations of the cover. The downward deflection distance was approximately 0.005 inches under an applied force of approximately 3 ounces. A 9-volt square wave driving signal was used with 0.2 second duration pulses every second. The resulting higher frequency cover deflection induced light intensity fluctuations that were superimposed as tiny ripples on the relatively lower frequency scatter curve and could be observed as a tiny ripple without obscuring the signal. The endpoint, however, appeared sooner than that observed in Example 1 and was occasionally sharper.

EXAMPLE 8

Plasminogen Activator Assay

A reaction slide was prepared as in Example 1 but filled with a mixture for measuring quantitatively the concentration of plasminogen activator in a sample. The assay method of Campbell was adapted accordingly: E. E. Campbell, et al. (Clinical Chemistry 28, No. 5, 1982, pp. 1125-1128). The mixture consisted of 25 parts (by volume) 0.33 mg/ml plasminogen in 0.1 M sodium phosphate buffer; 20 parts S-2251 (D-Val-Leu-Lys-$p$nitroanilide) 75 mM in deionized water; and 10 parts fibrin monomer 3.3 mg/ml in phosphate buffer/urea (0.02 M sodium phosphate, 0.3 M sodium chloride, and 3 M urea). After filling, the reaction slide was freeze-dried. After freeze-drying the reagents in the reaction volume, the slide was tested as follows: A sample of plasminogen activator was added to the sample well of a reaction slide prewarmed to 37° C. The sample contained 1000 units of activator in TRIS buffer (50 mM Tris, 150 mM sodium chloride, pH 7.4). After a few minutes, a bright yellow color appeared, indicating the presence of activator. This visually apparent color could easily be seen or readily monitored by placing the slide against a white reflective background (reflectance measurement). Alternatively, the color could be read colorimetrically via absorbance.

Obviously, numerous modifications and variations of the present invention are possible in light of the above teachings. It is therefore to be understood that within the scope of the appended claims, the invention may be practiced otherwise than as specifically described therein.

What is claimed as new and desired to be secured by Letters Patent of the United States is:

1. An analytical system for performing a prothrombin time assay comprising:
   (i) a reaction slide bearing (1) a sample well for receiving a liquid sample and (2) a reaction chamber containing a dry reagent matrix in which is embedded a plurality of magnetic particles distributed homogeneously therethrough, wherein said reagent is one member selected from the group consisting of prothrombin time assay reagents;
   (ii) said sample well and said reaction chamber being in fluid connection through a transport zone of geometry such that a volume of liquid sample placed in said reaction chamber is transported from said sample well to said reaction chamber simultaneously,
   (iii) means for optically monitoring said reaction chamber,
   (iv) means for subjecting said reaction chamber to an oscillating magnetic field,
   (v) whereby, when said sample is introduced into said reaction chamber, said dry reagent matrix is solubilized and said magnetic particles are thereby freed to move in an oscillating pattern induced by said osicllating magnetic field, thus providing a start and a stop time for said prothrombin time assay, corresponding to a change in the degree of said magnetic particle movement relative to said magnetic field.

2. The analytical system of claim 1, wherein said magnetic particles are magnetite.

3. The analytical system of claim 1, further comprising a means for subjecting said reaction chamber to a permanent magnetic field.

4. The analytical system of claim 1, wherein said means for subjecting said reaction chamber to an osicllating magnetic field is an electromagnet.

5. The analytical system of claim 3, wherein said means for subjecting said reaction chamber to a permanent magnetic field is a permanent magnet.

6. The analytical system of claim 1, wherein said means for monitoring said reaction chamber comprises means for impinging light onto said reaction chamber and means for detecting light reflected from said reaction chamber.

7. The analytical system of claim 1, wherein said dry reagent matrix in which is embedded a plurality of magnetic particles is obtained by adding to said reaction chamber a slurry of reagent and magnetic particles and freeze drying same.

8. The analytical system of claim 7, wherein said magnetic aparticles are present in said slurry in an amount of 5 to 50 milligrams per milliliter.

9. The analytical system of claim 1, wherein said reagent comprises a combination of thromplastin and calcium chloride.

10. A method for performing a prothrombin time assay, comprising:
    (i) subjecting to an oscillating magnetic field a reaction slide bearing (1) a sample well for receiving a liquid sample and (2) a reaction chamber containing a dry reagent matrix in which is embedded a plurality of magnetic particles distributed homogeneously therethrough, wherein said reagent is one member selected from the group consisting of prothrombin time assay reagents;
    said sample well and reaction chamber being in fluid connection through a transport zone of geometry such that a volume of liquid analyte sample placed in said sample well and corresponding to the volume of said reaction chamber is transported from said sample well to said reaction chamber simultaneously;
    (ii) adding a whole blood or plasma sample to said sample well whereby said sample is introduced simultaneously to said reaction chamber, said reagent is solubilized and said particles are freed to move in an oscillating pattern induced by said oscillating magnetic field; and (iii) optically monitoring said reaction chamber to measure a start time and a stop time for said prothrombin time assay, corresponding to a change in the degree of said particle movement relative to said magnetic field.

11. The method of claim 10, wherein said magnetic particles are magnetite.

12. The method of claim 10, wherein said reaction chamber is subjected to a permanent magnetic field.

13. The method of claim 10, wherein said reaction chamber is optically monitored by impinging light thereon and detecting light reflected from said reaction chamber.

14. The method of claim 10, wherein said sample is a whole blood sample.

15. The method of claim 10, wherein said sample is a plasma sample.

16. The method of claim 10, wherein said reagent comprises thromboplastin and calcium chloride.

* * * * *

UNITED STATES PATENT AND TRADEMARK OFFICE
CERTIFICATE OF CORRECTION

PATENT NO. : 4,849,340
DATED : July 18, 1989
INVENTOR(S) : BRUCE OBERHARDT

It is certified that error appears in the above-identified patent and that said Letters Patent is hereby corrected as shown below:

Column 40, line 6, after "said" please insert --sample well and corresponding to the volume of said--.

Signed and Sealed this

Thirty-first Day of December, 1991

Attest:

HARRY F. MANBECK, JR.

Attesting Officer     Commissioner of Patents and Trademarks